(12) United States Patent
Tarasova et al.

(10) Patent No.: US 9,475,839 B2
(45) Date of Patent: Oct. 25, 2016

(54) PEPTIDE-BASED INHIBITOR OF INTERLEUKIN-10 OR INTERFERON-GAMMA SIGNALING

(75) Inventors: Nadya I. Tarasova, Frederick, MD (US); Giorgio Trinchieri, Potomac, MD (US); Howard A. Young, North Potomac, MD (US); C. Andrew Stewart, Frederick, MD (US); Marco A. Cardone, Frederick, MD (US); Alan O. Perantoni, Fairfield, PA (US)

(73) Assignee: THE UNITED STATES OF AMERICA, AS REPRESENTED BY THE SECRETARY, DEPARTMENT OF HEALTH AND HUMAN SERVICES, Washington, DC (US)

( * ) Notice: Subject to any disclaimer, the term of this patent is extended or adjusted under 35 U.S.C. 154(b) by 599 days.

(21) Appl. No.: 13/697,259

(22) PCT Filed: May 11, 2011

(86) PCT No.: PCT/US2011/036010
§ 371 (c)(1),
(2), (4) Date: Dec. 19, 2012

(87) PCT Pub. No.: WO2011/143280
PCT Pub. Date: Nov. 17, 2011

(65) Prior Publication Data
US 2013/0109619 A1    May 2, 2013

Related U.S. Application Data

(60) Provisional application No. 61/333,512, filed on May 11, 2010.

(51) Int. Cl.
| C07K 7/08 | (2006.01) |
| C07K 14/00 | (2006.01) |
| C07K 7/06 | (2006.01) |
| C07K 14/47 | (2006.01) |
| C07K 14/715 | (2006.01) |

(52) U.S. Cl.
CPC .  C07K 7/08 (2013.01); C07K 7/06 (2013.01); C07K 14/001 (2013.01); C07K 14/4703 (2013.01); C07K 14/7155 (2013.01); C07K 14/7156 (2013.01)

(58) Field of Classification Search
CPC .. A61K 2300/00; A61K 38/00; A61K 38/17; A61K 2039/55527; A61K 38/2066; A61K 2039/55516; A61K 38/1793; C07K 16/244; C07K 16/2863; C07K 14/7155; C07K 2317/73; C07K 14/52; C07K 14/5428
See application file for complete search history.

(56) References Cited

U.S. PATENT DOCUMENTS

| 5,451,658 | A |   | 9/1995 | Seelig |
| 5,459,046 | A | * | 10/1995 | Kodama ............... C07K 14/80 435/252.33 |
| 5,582,999 | A |   | 12/1996 | Schreiber et al. |
| 5,731,155 | A |   | 3/1998 | Schreiber et al. |
| 6,682,898 | B2 |   | 1/2004 | Wu et al. |
| 6,683,052 | B1 |   | 1/2004 | Thiam et al. |
| 7,393,523 | B2 |   | 7/2008 | Zagury |
| 2006/0018923 | A1 | * | 1/2006 | Yuen et al. ................ 424/199.1 |

FOREIGN PATENT DOCUMENTS

| WO | WO9511312 A1 * | 4/1995 | ............... C12Q 1/00 |
| WO | WO9746585 A2 * | 6/1997 | ........... C07K 14/575 |
| WO | WO2008003066 A2 * | 1/2008 | |

OTHER PUBLICATIONS

Leite et al. *Leptodactylus ocellatus* (Amphibia): mechanism of defense in the skin and molecular phylogenetic relationships. J Exp Zool a Ecol Genet Physiol. Jan. 2010 1;313(1):1-8.*
Ahmed et al., "Peptide Mimetics of Gamma Interferon Possess Antiviral Properties against Vaccinia Virus and Other Viruses in the Presence of Poxvirus B8R Protein," *J. Virol.*, 79 (9), 5632-5639 (2005).
Diaz-Valdes et al., "Restoration of Functional Properties of Dendritic Cells using Peptide Inhibitors of Interleukin 10: Application to Hepatitis C Virus Infection," *J. Hepatology*, 50 (892 abstract), S324 (2009).
Diaz-Valdes et al., "Improved Dendritic cell-based immunization against Hepatitis C Virus using a Peptide Inhibitor of Interleukin 10," *J. Hepatology*, 52 (436 abstract), S177 (2010).
Diaz-Valdes et al., "Improved Dendritic Cell-Based Immunization Against Hepatitis C Virus Using Peptide Inhibitors of Interleukin 10," *J. Hepatology*, 53 (1), 23-31 (2011).
Edwards et al., "Bioinformatic discovery of novel bioactive peptide," *Nature Chem. Biol.*, 3 (2), 108-112 (2007).
Fischer, "The Design, Synthesis and Application of Stereochemical and Directional Peptide Isomers: A Critical Review," *Curr. Prot. Pep. Sci.*, 4 (5), 339-356 (2003).
International Search Report, Application No. PCT/US2011/036010, dated Dec. 14, 2011.
Johannessen et al., "Peptide structure stabilization by membrane anchoring and its general applicability to the development of potent cell-permeable inhibitors," *ChemBioChem.*, 12 (6), 914-921 (2011).
Jones et al., "Crystal structure of human cytomegalovirus IL-10 bound to soluble human IL-10R1," *PNAS.*, 99 (14), 9404-9409 (2002).
Remsberg et al., "Structural analogues of smoothened intracellular loops as potent inhibitors of Hedgehog pathway and cancer cell growth," *J. Med. Chem.*, 50 (18), 4534-4538 (2007).
Tarasova, "Preface," *Curr. Pharmaceutical. Design*, 10 (19), 3pp (2004).

(Continued)

*Primary Examiner* — Satyanarayana R Gudibande
*Assistant Examiner* — Jia-Hai Lee
(74) *Attorney, Agent, or Firm* — Bryan D. Zerhusen; Locke Lord LLP

(57) ABSTRACT

A peptide or peptidomimetic comprising an amino acid sequence based on conserved regions of IL10 or IFN-gamma receptor sequences, and related compounds and compositions, as well as methods for the use thereof to inhibit cytokine signaling.

20 Claims, 2 Drawing Sheets

(56) References Cited

OTHER PUBLICATIONS

Thompson-Snipes et al., "Interleukin 10: a novel stimulatory factor for mast cells and their progenitors," *J. Exp. Med.*, 173 (2), 507-510 (1991).
Timofeeva et al., "Rationally designed inhibitors identify STAT3 N-domain as a promising anticancer drug target," *ACN Chem. Biol.*, 2 (12), 799-809 (2007).
UniGene Accession No. Hs.856 (printed Nov. 9, 2012).
UniGene Accession No. Hs.193717 (printed Nov. 9, 2012).
UniGene Accession No. Hs.463059 (printed Nov. 9, 2012).
UniGene Accession No. Hs.504035 (printed Nov. 9, 2012).
UniGene Accession No. Hs.520414 (printed Nov. 9, 2012).
UniGene Accession No. Hs.634632 (printed Nov. 9, 2012).
UniGene Accession No. Hs.642990 (printed Nov. 9, 2012).
UniGene Accession No. Hs.654593 (printed Nov. 9, 2012).
Usacheva et al., "Contribution of the Box 1 and Box 2 Motifs of Cytokine Receptors to Jak1 Association and Activation," *J. Biol. Chem.*, 277 (50), 48220-48226 (2002).
Yoon et al., "Same structure, different function crystal structure of the Epstein-Barr virus IL-10 bound to the soluble IL-10R1 chain," *Structure*, 13 (4), 551-564 (2005).
Zdanov et al., "Crystal structure of human interleukin-10 at 1.6 Å resolution and a model of a complex with its soluble receptor," *Protein Sci.*, 5 (10), 1955-1962 (1996).

\* cited by examiner

SEQUENCE LISTING

```
<160> NUMBER OF SEQ ID NOS: 110

<210> SEQ ID NO 1
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 1

Xaa Val Leu Xaa Phe Xaa Lys
1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic

<400> SEQUENCE: 2

Ser Val Leu Leu Phe Lys Lys
1               5

<210> SEQ ID NO 3
<211> LENGTH: 17
<212> TYPE: PRT
<213> ORGANISM: Artificial Sequence
<220> FEATURE:
<223> OTHER INFORMATION: Synthetic

<400> SEQUENCE: 3

Leu Tyr Val Arg Arg Arg Lys Lys Leu Pro Ser Val Leu Leu Phe Lys
1               5                   10                  15
```

Lys

```
<210> SEQ ID NO 4
<211> LENGTH: 13
<212> TYPE: PRT
<213> ORGANISM: Artificial Sequence
<220> FEATURE:
<223> OTHER INFORMATION: Synthetic

<400> SEQUENCE: 4

Lys Lys Leu Pro Ser Val Leu Leu Phe Lys Lys Pro Ser
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Synthetic

<400> SEQUENCE: 5

Ser Pro Lys Lys Phe Leu Leu Val Ser Pro Leu Lys Lys
1               5                   10

<210> SEQ ID NO 6
<211> LENGTH: 11
<212> TYPE: PRT
<213> ORGANISM: Artificial Sequence
<220> FEATURE:
<223> OTHER INFORMATION: Synthetic

<400> SEQUENCE: 6

Lys Lys Phe Leu Leu Val Ser Pro Leu Lys Lys
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Synthetic

<400> SEQUENCE: 7

Pro Lys Lys Phe Leu Leu Val Ser Pro Leu Lys Lys
1               5                   10

<210> SEQ ID NO 8
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 8

Leu His Gly Ser Thr Xaa Ser Gly Phe Gly Ser Xaa Lys Pro Ser Leu
1               5                   10                  15
```

Gln Xaa

<210> SEQ ID NO 9
<211> LENGTH: 18
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 9

Leu His Gly Ser Thr Xaa Ser Gly Phe Gly Ser Thr Lys Pro Ser Leu
1               5                   10                  15

Gln Thr

<210> SEQ ID NO 10
<211> LENGTH: 18
<212> TYPE: PRT
<213> ORGANISM: Artificial Sequence
<220> FEATURE:
<223> OTHER INFORMATION: Synthetic

<400> SEQUENCE: 10

Leu His Gly Ser Thr Asp Ser Gly Phe Gly Ser Thr Lys Pro Ser Leu
1               5                   10                  15

Gln Thr

<210> SEQ ID NO 11
<211> LENGTH: 21
<212> TYPE: PRT
<213> ORGANISM: Artificial Sequence
<220> FEATURE:
<223> OTHER INFORMATION: Synthetic

<400> SEQUENCE: 11

Glu Glu Thr Gln Leu Ser Pro Lys Thr Ser Gly Phe Gly Ser Asp Thr
1               5                   10                  15

Ser Gly His Leu Lys
            20

<210> SEQ ID NO 12
<211> LENGTH: 20
<212> TYPE: PRT
<213> ORGANISM: Artificial Sequence
<220> FEATURE:
<223> OTHER INFORMATION: Synthetic

<400> SEQUENCE: 12

Glu Thr Gln Leu Ser Pro Lys Thr Ser Gly Phe Gly Ser Asp Thr Ser
1               5                   10                  15

Gly His Leu Lys
            20

<210> SEQ ID NO 13
<211> LENGTH: 19
<212> TYPE: PRT
<213> ORGANISM: Artificial Sequence
<220> FEATURE:
<223> OTHER INFORMATION: Synthetic

<400> SEQUENCE: 13

Thr Gln Leu Ser Pro Lys Thr Ser Gly Phe Gly Ser Asp Thr Ser Gly
1               5                   10                  15

His Leu Lys

<210> SEQ ID NO 14
<211> LENGTH: 19
<212> TYPE: PRT
<213> ORGANISM: Artificial Sequence
<220> FEATURE:
<223> OTHER INFORMATION: Synthetic

<400> SEQUENCE: 14

Lys Thr Gln Leu Ser Pro Lys Thr Ser Gly Phe Gly Ser Asp Thr Ser
1               5                   10                  15

Gly His Leu

<210> SEQ ID NO 15
<211> LENGTH: 21
<212> TYPE: PRT
<213> ORGANISM: Artificial Sequence
<220> FEATURE:
<223> OTHER INFORMATION: Synthetic

<400> SEQUENCE: 15

Lys Glu Glu Thr Gln Leu Ser Pro Lys Thr Ser Gly Phe Gly Ser Asp
1               5                   10                  15

Thr Ser Gly His Leu
            20

<210> SEQ ID NO 16
<211> LENGTH: 19
<212> TYPE: PRT
<213> ORGANISM: Artificial Sequence
<220> FEATURE:
<223> OTHER INFORMATION: Synthetic

<400> SEQUENCE: 16

Lys Thr Gln Leu Ser Pro Lys Thr Ser Gly Phe Gly Ser Asn Thr Ser
1               5                   10                  15

Gly His Leu

<210> SEQ ID NO 17
<211> LENGTH: 8
<212> TYPE: PRT
<213> ORGANISM: Artificial Sequence
<220> FEATURE:
<223> OTHER INFORMATION: Synthetic

<400> SEQUENCE: 17

Thr Asp Ser Gly Ile Cys Leu Gln
1               5

<210> SEQ ID NO 18
<211> LENGTH: 14
<212> TYPE: PRT
<213> ORGANISM: Artificial Sequence
<220> FEATURE:
<223> OTHER INFORMATION: Synthetic

<400> SEQUENCE: 18

Lys Thr Cys Gly Asp Asn Thr Asp Ser Gly Ile Cys Leu Gln
1               5                   10

<210> SEQ ID NO 19

```
<211> LENGTH: 18
<212> TYPE: PRT
<213> ORGANISM: Artificial Sequence
<220> FEATURE:
<223> OTHER INFORMATION: Synthetic

<400> SEQUENCE: 19

Lys Ser Cys Ser Ser Gly Ser Ser Asn Ser Thr Asp Ser Gly Ile Cys
1               5                   10                  15

Leu Gln

<210> SEQ ID NO 20
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (5)..(6)
<223> OTHER INFORMATION: Xaa can be any naturally occurring amino acid

<400> SEQUENCE: 20

Phe Xaa Gly Tyr Xaa Xaa Gln Thr Arg
1               5

<210> SEQ ID NO 21
<211> LENGTH: 9
<212> TYPE: PRT
<213> ORGANISM: Artificial Sequence
<220> FEATURE:
<223> OTHER INFORMATION: Synthetic

<400> SEQUENCE: 21

Phe Gln Gly Tyr Leu Arg Gln Thr Arg
1               5

<210> SEQ ID NO 22
<211> LENGTH: 10
<212> TYPE: PRT
<213> ORGANISM: Artificial Sequence
<220> FEATURE:
<223> OTHER INFORMATION: Synthetic

<400> SEQUENCE: 22

Lys Phe Gln Gly Tyr Leu Arg Gln Thr Arg
1               5                   10

<210> SEQ ID NO 23
<211> LENGTH: 10
<212> TYPE: PRT
<213> ORGANISM: Artificial Sequence
<220> FEATURE:
<223> OTHER INFORMATION: Synthetic

<400> SEQUENCE: 23

Ala Phe Gln Gly Tyr Leu Arg Gln Thr Arg
1               5                   10

<210> SEQ ID NO 24
<211> LENGTH: 10
<212> TYPE: PRT
<213> ORGANISM: Artificial Sequence
<220> FEATURE:
```

```
<223> OTHER INFORMATION: Synthetic

<400> SEQUENCE: 24

Arg Thr Gln Arg Leu Tyr Gly Gln Phe Lys
1               5                   10

<210> SEQ ID NO 25
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid

<400> SEQUENCE: 25

Ala Xaa Gly Tyr Leu Lys Gln
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic

<400> SEQUENCE: 26

Ala Lys Gly Tyr Leu Lys Gln
1               5

<210> SEQ ID NO 27
<211> LENGTH: 12
<212> TYPE: PRT
<213> ORGANISM: Artificial Sequence
<220> FEATURE:
<223> OTHER INFORMATION: Synthetic

<400> SEQUENCE: 27

Lys Pro Pro Ala Leu Ala Lys Gly Tyr Leu Lys Gln
1               5                   10

<210> SEQ ID NO 28
<211> LENGTH: 13
<212> TYPE: PRT
<213> ORGANISM: Artificial Sequence
<220> FEATURE:
<223> OTHER INFORMATION: Synthetic

<400> SEQUENCE: 28

Lys Pro Pro Ala Leu Ala Lys Gly Tyr Leu Lys Gln Glu
1               5                   10

<210> SEQ ID NO 29
<211> LENGTH: 8
<212> TYPE: PRT
<213> ORGANISM: Artificial Sequence
<220> FEATURE:
<223> OTHER INFORMATION: Synthetic

<400> SEQUENCE: 29

Lys Ala Lys Gly Tyr Leu Lys Gln
1               5

<210> SEQ ID NO 30
<211> LENGTH: 8
```

```
<212> TYPE: PRT
<213> ORGANISM: Artificial Sequence
<220> FEATURE:
<223> OTHER INFORMATION: Synthetic

<400> SEQUENCE: 30

Leu Ala Lys Gly Tyr Leu Lys Gln
1               5

<210> SEQ ID NO 31
<211> LENGTH: 10
<212> TYPE: PRT
<213> ORGANISM: Artificial Sequence
<220> FEATURE:
<223> OTHER INFORMATION: Synthetic

<400> SEQUENCE: 31

Leu Val Thr Leu Pro Leu Ile Ser Ser Leu
1               5                   10

<210> SEQ ID NO 32
<211> LENGTH: 15
<212> TYPE: PRT
<213> ORGANISM: Artificial Sequence
<220> FEATURE:
<223> OTHER INFORMATION: Synthetic

<400> SEQUENCE: 32

Lys Leu Val Thr Leu Pro Leu Ile Ser Ser Leu Gln Ser Ser Glu
1               5                   10                  15

<210> SEQ ID NO 33
<211> LENGTH: 12
<212> TYPE: PRT
<213> ORGANISM: Artificial Sequence
<220> FEATURE:
<223> OTHER INFORMATION: Synthetic

<400> SEQUENCE: 33

Lys Leu Val Thr Leu Pro Leu Ile Ser Ser Leu Gln
1               5                   10

<210> SEQ ID NO 34
<211> LENGTH: 11
<212> TYPE: PRT
<213> ORGANISM: Artificial Sequence
<220> FEATURE:
<223> OTHER INFORMATION: Synthetic

<400> SEQUENCE: 34

Lys Leu Val Thr Leu Pro Leu Ile Ser Ser Leu
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Synthetic

<400> SEQUENCE: 35

Lys Asn Leu Val Thr Leu Pro Leu Ile Ser Ser Leu
1               5                   10

<210> SEQ ID NO 36
<211> LENGTH: 8
<212> TYPE: PRT
```

```
<213> ORGANISM: Artificial Sequence
<220> FEATURE:
<223> OTHER INFORMATION: Synthetic
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 36

Pro Xaa His Leu Lys Glu Xaa Leu
1               5

<210> SEQ ID NO 37
<211> LENGTH: 12
<212> TYPE: PRT
<213> ORGANISM: Artificial Sequence
<220> FEATURE:
<223> OTHER INFORMATION: Synthetic

<400> SEQUENCE: 37

Leu Pro Gln His Leu Lys Glu Phe Leu Gly His Pro
1               5                   10

<210> SEQ ID NO 38
<211> LENGTH: 13
<212> TYPE: PRT
<213> ORGANISM: Artificial Sequence
<220> FEATURE:
<223> OTHER INFORMATION: Synthetic

<400> SEQUENCE: 38

Ser Glu Phe Asp Ile Phe Ile Asn Tyr Ile Glu Ala Tyr
1               5                   10

<210> SEQ ID NO 39
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid

<400> SEQUENCE: 39

Xaa Leu Pro Lys Ser Leu
1               5

<210> SEQ ID NO 40
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 40

Xaa Leu Pro Lys Ser Leu Xaa Ser Val Val
```

<210> SEQ ID NO 41
<211> LENGTH: 5
<212> TYPE: PRT
<213> ORGANISM: Artificial Sequence
<220> FEATURE:
<223> OTHER INFORMATION: Synthetic

<400> SEQUENCE: 41

Leu Pro Lys Ser Leu
1               5

<210> SEQ ID NO 42
<211> LENGTH: 5
<212> TYPE: PRT
<213> ORGANISM: Artificial Sequence
<220> FEATURE:
<223> OTHER INFORMATION: Synthetic

<400> SEQUENCE: 42

Ile Leu Pro Lys Ser
1               5

<210> SEQ ID NO 43
<211> LENGTH: 19
<212> TYPE: PRT
<213> ORGANISM: Artificial Sequence
<220> FEATURE:
<223> OTHER INFORMATION: Synthetic

<400> SEQUENCE: 43

Phe Tyr Ile Lys Lys Ile Asn Pro Leu Lys Glu Lys Ser Ile Ile Leu
1               5                   10                  15

Pro Lys Ser

<210> SEQ ID NO 44
<211> LENGTH: 18
<212> TYPE: PRT
<213> ORGANISM: Artificial Sequence
<220> FEATURE:
<223> OTHER INFORMATION: Synthetic

<400> SEQUENCE: 44

Pro Leu Lys Glu Lys Ser Ile Ile Leu Pro Lys Ser Leu Leu Ser Val
1               5                   10                  15

Val Arg

<210> SEQ ID NO 45
<211> LENGTH: 14
<212> TYPE: PRT
<213> ORGANISM: Artificial Sequence
<220> FEATURE:
<223> OTHER INFORMATION: Synthetic

<400> SEQUENCE: 45

Ile Leu Pro Lys Ser Leu Leu Ser Val Val Arg Ser Ala Thr
1               5                   10

<210> SEQ ID NO 46
<211> LENGTH: 17
<212> TYPE: PRT
<213> ORGANISM: Artificial Sequence
<220> FEATURE:
<223> OTHER INFORMATION: Synthetic

```
<400> SEQUENCE: 46

Lys Lys Glu Lys Ser Ile Ile Leu Pro Lys Ser Leu Ser Val Val
1               5                   10                  15

Arg

<210> SEQ ID NO 47
<211> LENGTH: 15
<212> TYPE: PRT
<213> ORGANISM: Artificial Sequence
<220> FEATURE:
<223> OTHER INFORMATION: Synthetic

<400> SEQUENCE: 47

Lys Lys Ser Ile Ile Leu Pro Lys Ser Leu Leu Ser Val Val Arg
1               5                   10                  15

<210> SEQ ID NO 48
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (5)..(5)
<223> OTHER INFORMATION: Xaa can be any naturally occurring amino acid

<400> SEQUENCE: 48

Tyr His Ser Arg Xaa
1               5

<210> SEQ ID NO 49
<211> LENGTH: 12
<212> TYPE: PRT
<213> ORGANISM: Artificial Sequence
<220> FEATURE:
<223> OTHER INFORMATION: Synthetic

<400> SEQUENCE: 49

Lys Ser Ile Ala Leu Asn Ser Tyr His Ser Arg Asn
1               5                   10

<210> SEQ ID NO 50
<211> LENGTH: 11
<212> TYPE: PRT
<213> ORGANISM: Artificial Sequence
<220> FEATURE:
<223> OTHER INFORMATION: Synthetic

<400> SEQUENCE: 50

Lys Leu Asn Ser Tyr His Ser Arg Asn Gly Ser
1               5                   10

<210> SEQ ID NO 51
<211> LENGTH: 9
<212> TYPE: PRT
<213> ORGANISM: Artificial Sequence
<220> FEATURE:
<223> OTHER INFORMATION: Synthetic

<400> SEQUENCE: 51

Lys Ser Tyr His Ser Arg Asn Gly Ser
1               5

<210> SEQ ID NO 52
<211> LENGTH: 6
```

<212> TYPE: PRT
<213> ORGANISM: Artificial Sequence
<220> FEATURE:
<223> OTHER INFORMATION: Synthetic

<400> SEQUENCE: 52

Gly Tyr Asp Lys Pro His
1               5

<210> SEQ ID NO 53
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 53

Gly Tyr Asp Lys Pro His Xaa
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 54

Gly Tyr Asp Lys Pro His Xaa Leu Val
1               5

<210> SEQ ID NO 55
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (7)..(7)
<223> OTHER INFORMATION: Xaa can be any naturally occurring amino acid

<400> SEQUENCE: 55

Gly Tyr Asp Lys Pro His Xaa Leu Val Asp
1               5                   10

<210> SEQ ID NO 56
<211> LENGTH: 15
<212> TYPE: PRT
<213> ORGANISM: Artificial Sequence
<220> FEATURE:
<223> OTHER INFORMATION: Synthetic

<400> SEQUENCE: 56

Lys Gly Tyr Asp Lys Pro His Val Leu Val Asp Leu Leu Val Asp
1               5                   10                  15

<210> SEQ ID NO 57
<211> LENGTH: 10
<212> TYPE: PRT
<213> ORGANISM: Artificial Sequence

```
<220> FEATURE:
<223> OTHER INFORMATION: Synthetic

<400> SEQUENCE: 57

Lys Gly Tyr Asp Lys Pro His Val Leu Val
1               5                   10

<210> SEQ ID NO 58
<211> LENGTH: 8
<212> TYPE: PRT
<213> ORGANISM: Artificial Sequence
<220> FEATURE:
<223> OTHER INFORMATION: Synthetic

<400> SEQUENCE: 58

Lys Gly Tyr Asp Lys Pro His Val
1               5

<210> SEQ ID NO 59
<211> LENGTH: 9
<212> TYPE: PRT
<213> ORGANISM: Artificial Sequence
<220> FEATURE:
<223> OTHER INFORMATION: Synthetic

<400> SEQUENCE: 59

Lys Phe Gly Tyr Asp Lys Pro His Val
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid

<400> SEQUENCE: 60

Gly Lys Glu Ser Leu Xaa Gly Tyr Arg
1               5

<210> SEQ ID NO 61
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (10)..(10)
<223> OTHER INFORMATION: Xaa can be any naturally occurring amino acid

<400> SEQUENCE: 61

Gly Lys Glu Ser Leu Xaa Gly Tyr Arg Xaa Thr
1               5                   10

<210> SEQ ID NO 62
<211> LENGTH: 12
<212> TYPE: PRT
<213> ORGANISM: Artificial Sequence
<220> FEATURE:
<223> OTHER INFORMATION: Synthetic
```

<400> SEQUENCE: 62

Lys Gly Lys Glu Ser Leu Ile Gly Tyr Arg Pro Thr
1               5                   10

<210> SEQ ID NO 63
<211> LENGTH: 11
<212> TYPE: PRT
<213> ORGANISM: Artificial Sequence
<220> FEATURE:
<223> OTHER INFORMATION: Synthetic

<400> SEQUENCE: 63

Lys Gly Gly Lys Glu Ser Leu Ile Gly Tyr Arg
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Synthetic

<400> SEQUENCE: 64

Lys Gly Lys Glu Ser Leu Ile Gly Tyr Arg
1               5                   10

<210> SEQ ID NO 65
<211> LENGTH: 6
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid

<400> SEQUENCE: 65

Xaa Pro Xaa Xaa Ile Pro
1               5

<210> SEQ ID NO 66
<211> LENGTH: 16
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (7)..(9)
<223> OTHER INFORMATION: Xaa can be any naturally occurring amino acid
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (14)..(15)

```
<223> OTHER INFORMATION: Xaa can be any naturally occurring amino acid

<400> SEQUENCE: 66

Xaa Pro Xaa Xaa Ile Pro Xaa Xaa Xaa Glu Xaa Tyr Leu Xaa Xaa Pro
1               5                   10                  15

<210> SEQ ID NO 67
<211> LENGTH: 18
<212> TYPE: PRT
<213> ORGANISM: Artificial Sequence
<220> FEATURE:
<223> OTHER INFORMATION: Synthetic

<400> SEQUENCE: 67

Lys Lys Tyr Gln Ser Arg Val Lys Tyr Trp Phe Gln Ala Pro Pro Asn
1               5                   10                  15

Ile Pro

<210> SEQ ID NO 68
<211> LENGTH: 17
<212> TYPE: PRT
<213> ORGANISM: Artificial Sequence
<220> FEATURE:
<223> OTHER INFORMATION: Synthetic

<400> SEQUENCE: 68

Lys Ala Pro Pro Asn Ile Pro Glu Gln Ile Glu Glu Tyr Leu Lys Asp
1               5                   10                  15

Pro

<210> SEQ ID NO 69
<211> LENGTH: 22
<212> TYPE: PRT
<213> ORGANISM: Artificial Sequence
<220> FEATURE:
<223> OTHER INFORMATION: Synthetic

<400> SEQUENCE: 69

Val Gln Arg Lys Ala Ile His Glu Leu Ile Gln Val Met Ala Glu Leu
1               5                   10                  15

Ser Pro Ala Ala Lys Thr
            20

<210> SEQ ID NO 70
<211> LENGTH: 13
<212> TYPE: PRT
<213> ORGANISM: Artificial Sequence
<220> FEATURE:
<223> OTHER INFORMATION: Synthetic

<400> SEQUENCE: 70

Lys Leu Asn Ser Tyr His Ser Arg Asn Gly Ser Glu Ser
1               5                   10

<210> SEQ ID NO 71
<211> LENGTH: 11
<212> TYPE: PRT
<213> ORGANISM: Artificial Sequence
<220> FEATURE:
<223> OTHER INFORMATION: Synthetic

<400> SEQUENCE: 71

Gly Lys Glu Ser Leu Ile Gly Tyr Arg Pro Thr
1               5                   10
```

<210> SEQ ID NO 72
<211> LENGTH: 13
<212> TYPE: PRT
<213> ORGANISM: Artificial Sequence
<220> FEATURE:
<223> OTHER INFORMATION: Synthetic

<400> SEQUENCE: 72

Leu His Gly Ser Thr Asp Ser Gly Phe Gly Ser Thr Lys
1               5                   10

<210> SEQ ID NO 73
<211> LENGTH: 13
<212> TYPE: PRT
<213> ORGANISM: Artificial Sequence
<220> FEATURE:
<223> OTHER INFORMATION: Synthetic

<400> SEQUENCE: 73

Ser Glu Phe Asp Ile Phe Ile Asn Tyr Ile Glu Ala Tyr
1               5                   10

<210> SEQ ID NO 74
<211> LENGTH: 24
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (4)..(4)
<223> OTHER INFORMATION: Xaa is norleucine.
<220> FEATURE:
<221> NAME/KEY: misc_feature
<222> LOCATION: (18)..(18)
<223> OTHER INFORMATION: Xaa is norleucine.
<220> FEATURE:
<221> NAME/KEY: misc_feature
<222> LOCATION: (20)..(20)
<223> OTHER INFORMATION: Xaa is norleucine.

<400> SEQUENCE: 74

Tyr Lys Ala Xaa Ser Glu Phe Asp Ile Phe Ile Asn Tyr Ile Glu Ala
1               5                   10                  15

Tyr Xaa Thr Xaa Lys Ile Arg Asn
            20

<210> SEQ ID NO 75
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 75

Leu His Gly Ser Thr Xaa Ser Gly Phe Gly Ser Xaa Lys
1               5                   10

<210> SEQ ID NO 76
<211> LENGTH: 342
<212> TYPE: PRT

<213> ORGANISM: Homo sapiens

<400> SEQUENCE: 76

Ile Ile Phe Phe Ala Phe Val Leu Leu Leu Ser Gly Ala Leu Ala Tyr
1               5                   10                  15

Cys Leu Ala Leu Gln Leu Tyr Val Arg Arg Arg Lys Lys Leu Pro Ser
            20                  25                  30

Val Leu Leu Phe Lys Lys Pro Ser Pro Phe Ile Phe Ile Ser Gln Arg
        35                  40                  45

Pro Ser Pro Glu Thr Gln Asp Thr Ile His Pro Leu Asp Glu Glu Ala
    50                  55                  60

Phe Leu Lys Val Ser Pro Glu Leu Lys Asn Leu Asp Leu His Gly Ser
65                  70                  75                  80

Thr Asp Ser Gly Phe Gly Ser Thr Lys Pro Ser Leu Gln Thr Glu Glu
                85                  90                  95

Pro Gln Phe Leu Leu Pro Asp Pro His Pro Gln Ala Asp Arg Thr Leu
            100                 105                 110

Gly Asn Gly Glu Pro Pro Val Leu Gly Asp Ser Cys Ser Ser Gly Ser
        115                 120                 125

Ser Asn Ser Thr Asp Ser Gly Ile Cys Leu Gln Glu Pro Ser Leu Ser
    130                 135                 140

Pro Ser Thr Gly Pro Thr Trp Glu Gln Gln Val Gly Ser Asn Ser Arg
145                 150                 155                 160

Gly Gln Asp Asp Ser Gly Ile Asp Leu Val Gln Asn Ser Glu Gly Arg
                165                 170                 175

Ala Gly Asp Thr Gln Gly Gly Ser Ala Leu Gly His His Ser Pro Pro
            180                 185                 190

Glu Pro Glu Val Pro Gly Glu Asp Pro Ala Ala Val Ala Phe Gln
        195                 200                 205

Gly Tyr Leu Arg Gln Thr Arg Cys Ala Glu Glu Lys Ala Thr Lys Thr
    210                 215                 220

Gly Cys Leu Glu Glu Glu Ser Pro Leu Thr Asp Gly Leu Gly Pro Lys
225                 230                 235                 240

Phe Gly Arg Cys Leu Val Asp Glu Ala Gly Leu His Pro Ala Leu
                245                 250                 255

Ala Lys Gly Tyr Leu Lys Gln Asp Pro Leu Glu Met Thr Leu Ala Ser
            260                 265                 270

Ser Gly Ala Pro Thr Gly Gln Trp Asn Gln Pro Thr Glu Glu Trp Ser
        275                 280                 285

Leu Leu Ala Leu Ser Ser Cys Ser Asp Leu Gly Ile Ser Asp Trp Ser
    290                 295                 300

Phe Ala His Asp Leu Ala Pro Leu Gly Cys Val Ala Ala Pro Gly Gly
305                 310                 315                 320

Leu Leu Gly Ser Phe Asn Ser Asp Leu Val Thr Leu Pro Leu Ile Ser
                325                 330                 335

Ser Leu Gln Ser Ser Glu
            340

<210> SEQ ID NO 77
<211> LENGTH: 339
<212> TYPE: PRT
<213> ORGANISM: Ailuropoda melanoleuca

<400> SEQUENCE: 77

Ser Ile Phe Phe Ile Phe Val Leu Leu Leu Cys Gly Ala Leu Ala Tyr

```
                1               5                   10                  15
            Cys Leu Ala Leu His Leu Tyr Val Arg Arg Lys Lys Leu Pro Ser
                            20                  25                  30

Val Leu Val Phe Glu Lys Pro Gln Pro Ser Ser Phe Val Ser Gln Leu
                            35                  40                  45

Pro Cys Pro Glu Pro Gln Asp Ala Ile His Leu Leu Asp Glu Glu Ala
                50                      55                  60

Phe Pro Lys Val Ser Pro Glu Leu Lys Asn Ser Glu Leu His Gly Ser
            65                      70                  75                  80

Thr Asp Ser Gly Phe Gly Ser Ala Lys Pro Ser Leu Gln Asn Glu Glu
                            85                  90                  95

Pro Gln Phe Leu Leu Pro Ala Pro His Pro Gln Ala Gly Gly Thr Val
                            100                 105                 110

Gly Lys Gly Ala Pro Leu Glu Leu Glu Ser Ser Cys Ser Gly Gly Ser
                            115                 120                 125

Ser Thr Asp Ser Gly Ile Cys Leu Gln Glu Pro Arg Leu Ser Pro Gly
                130                     135                 140

Thr Gly Pro Ser Trp Lys Gln Val Gly Asn Ser Ser Gln Asp Gln
            145                     150                 155                 160

Asp Asp Ser Gly Ile Gly Leu Val Gln Asn Ser Glu Gly Gln Pro Gly
                            165                 170                 175

Asp Gly Gln Gly Gly Ser Ala Leu Gly His Val Asn Pro Pro Gly Pro
                            180                 185                 190

Glu Ala Ser Gly Glu Glu Asp Pro Asp Ser Val Ala Phe Arg Gly Tyr
                            195                 200                 205

Leu Lys Gln Thr Arg Cys Thr Glu Glu Lys Ala Ala Lys Thr Gly Cys
                210                     215                 220

Leu Glu Glu Glu Ser Ser Ser Thr Asp Ser Leu Gly Pro Lys Phe Arg
            225                     230                 235                 240

Thr Cys Leu Asp Ala Glu Ala Gly Trp Pro Pro Val Pro Ala Lys
                            245                 250                 255

Gly Tyr Leu Lys Gln Asp Pro Gly Met Thr Val Thr Pro Ser Gly Thr
                            260                 265                 270

Ser Thr Gly Gln Trp Asp Gln Pro Met Glu Glu Trp Ser Leu Leu Gly
                            275                 280                 285

Leu Thr Ser Cys Gly Asp Leu Gly Glu Ser Asp Trp Ser Leu Ala His
                            290                 295                 300

Asp Leu Ala Ser Leu Asp Cys Leu Ala Ala Pro Gly Ser Leu Leu Gly
            305                     310                 315                 320

Ser Phe Asp Ser Asn Leu Val Thr Leu Pro Leu Ile Ser Ser Leu His
                            325                 330                 335

Ser Asn Glu

<210> SEQ ID NO 78
<211> LENGTH: 336
<212> TYPE: PRT
<213> ORGANISM: Mus musculus

<400> SEQUENCE: 78

Ser Ile Leu Val Ile Ser Met Leu Leu Phe Cys Gly Ile Leu Val Cys
            1               5                   10                  15

Leu Val Leu Gln Trp Tyr Ile Arg His Pro Gly Lys Leu Pro Thr Val
                            20                  25                  30

Leu Val Phe Lys Lys Pro His Asp Phe Phe Pro Ala Asn Pro Leu Cys
```

```
                 35                 40                 45
Pro Glu Thr Pro Asp Ala Ile His Ile Val Asp Leu Glu Val Phe Pro
         50                 55                 60
Lys Val Ser Leu Glu Leu Arg Asp Ser Val Leu His Gly Ser Thr Asp
 65                 70                 75                 80
Ser Gly Phe Gly Gly Lys Pro Ser Leu Gln Thr Glu Glu Ser Gln
                 85                 90                 95
Phe Leu Leu Pro Gly Ser His Pro Gln Ile Gln Gly Thr Leu Gly Lys
                100                105                110
Glu Glu Ser Pro Gly Leu Gln Ala Thr Cys Gly Asp Asn Thr Asp Ser
            115                120                125
Gly Ile Cys Leu Gln Glu Pro Gly Leu His Ser Ser Met Gly Pro Ala
        130                135                140
Trp Lys Gln Gln Leu Gly Tyr Thr His Gln Asp Gln Asp Ser Asp
145                150                155                160
Val Asn Leu Val Gln Asn Ser Pro Gly Gln Pro Lys Tyr Thr Gln Asp
                165                170                175
Ala Ser Ala Leu Gly His Val Cys Leu Leu Glu Pro Lys Ala Pro Glu
            180                185                190
Glu Lys Asp Gln Val Met Val Thr Phe Gln Gly Tyr Gln Lys Gln Thr
        195                200                205
Arg Trp Lys Ala Glu Ala Ala Gly Pro Ala Glu Cys Leu Asp Glu Glu
    210                215                220
Ile Pro Leu Thr Asp Ala Phe Asp Pro Glu Leu Gly Val His Leu Gln
225                230                235                240
Asp Asp Leu Ala Trp Pro Pro Ala Leu Ala Ala Gly Tyr Leu Lys
                245                250                255
Gln Glu Ser Gln Gly Met Ala Ser Ala Pro Pro Gly Thr Pro Ser Arg
            260                265                270
Gln Trp Asn Gln Leu Thr Glu Glu Trp Ser Leu Leu Gly Val Val Ser
        275                280                285
Cys Glu Asp Leu Ser Ile Glu Ser Trp Arg Phe Ala His Lys Leu Asp
    290                295                300
Pro Leu Asp Cys Gly Ala Ala Pro Gly Gly Leu Leu Asp Ser Leu Gly
305                310                315                320
Ser Asn Leu Val Thr Leu Pro Leu Ile Ser Ser Leu Gln Val Glu Glu
                325                330                335

<210> SEQ ID NO 79
<211> LENGTH: 331
<212> TYPE: PRT
<213> ORGANISM: Rattus norvegicus

<400> SEQUENCE: 79

Ser Ile Phe Phe Leu Ser Ile Leu Ile Leu Cys Gly Ala Leu Val Cys
 1               5                 10                15
Leu Val Leu Leu Trp Tyr Ile Arg His Pro Gly Lys Leu Pro Ala Val
                20                 25                30
Leu Val Phe Glu Lys Pro Pro Asp Phe Leu Leu Ala Asn Pro Arg Cys
            35                 40                 45
Pro Glu Thr Leu Asp Asp Ile His Ile Leu Asp Leu Glu Ala Phe Pro
        50                 55                 60
Lys Val Ser Pro Glu Leu Lys Asp Ser Asp Leu His Gly Ser Thr Asp
 65                 70                 75                 80
```

Ser Gly Phe Gly Ser Gly Lys Pro Ser Leu Gln Thr Glu Glu Ser Gln
            85                  90                  95

Phe Phe Leu Leu Asp Ser His Ala Gln Ile Gln Glu Thr Leu Gly Lys
        100                 105                 110

Glu Gly Ser Ser Glu Leu Gln Asp Thr Cys Gly Asp Asn Thr Asp Ser
        115                 120                 125

Gly Ile Cys Leu Gln Glu Ser Ser Leu His Ser Ser Met Gly Pro Pro
130                 135                 140

Trp Lys Gln Gln Phe Gly Tyr Thr His Gln Asp Gln Asp Asp Ser Asp
145                 150                 155                 160

Leu Val Gln Asn Ser Pro Gly His Pro Lys His Thr Gln Asp Gly Ser
                165                 170                 175

Ala Leu Gly His Gly Cys Leu Leu Glu Pro Glu Val Pro Glu Glu Lys
            180                 185                 190

Asp Gln Val Met Val Thr Phe Gln Gly Tyr Gln Lys Gln Thr Arg Trp
        195                 200                 205

Lys Glu Glu Ala Ala Glu Pro Leu Asp Gly Ile Pro Leu Ala Glu
    210                 215                 220

Ala Phe Asp Pro Glu Leu Gly Val Arg Leu Gln Gly Asp Ser Ala Trp
225                 230                 235                 240

Pro Pro Val Ala Leu Ala Thr Gly Tyr Leu Lys Gln Glu Ser Gln Gly
                245                 250                 255

Met Ala Ser Ala Pro Pro Gly Thr Pro Ser Arg Gln Trp Asn Gln Leu
            260                 265                 270

Ala Glu Glu Ser Ser Leu Leu Gly Val Val Ser Cys Glu Asp Leu Ser
        275                 280                 285

Ile Glu Ser Leu Gly Phe Ala His Glu Leu Val Pro Leu Asp Cys Gly
    290                 295                 300

Ala Ala Ser Ser Gly Leu Leu Asp Ser Leu Gly Thr Asn Leu Val Thr
305                 310                 315                 320

Leu Pro Leu Ile Ser Ser Leu Gln Ile Glu Glu
                325                 330

<210> SEQ ID NO 80
<211> LENGTH: 260
<212> TYPE: PRT
<213> ORGANISM: Homo sapiens

<400> SEQUENCE: 80

Lys Ser Lys Glu Val Cys Ile Thr Ile Phe Asn Ser Ser Ile Lys Gly
1               5                   10                  15

Ser Leu Trp Ile Pro Val Val Ala Ala Leu Leu Leu Phe Leu Val Leu
            20                  25                  30

Ser Leu Val Phe Ile Cys Phe Tyr Ile Lys Lys Ile Asn Pro Leu Lys
        35                  40                  45

Glu Lys Ser Ile Ile Leu Pro Lys Ser Leu Ile Ser Val Val Arg Ser
    50                  55                  60

Ala Thr Leu Glu Thr Lys Pro Glu Ser Lys Tyr Val Ser Leu Ile Thr
65                  70                  75                  80

Ser Tyr Gln Pro Phe Ser Leu Gly Lys Glu Val Val Cys Glu Glu Pro
                85                  90                  95

Leu Ser Pro Ala Thr Val Pro Gly Met His Thr Glu Asp Asn Pro Gly
            100                 105                 110

Lys Val Glu His Thr Glu Glu Leu Ser Ser Ile Thr Glu Val Val Thr
        115                 120                 125

```
Thr Glu Glu Asn Ile Pro Asp Val Pro Gly Ser His Leu Thr Pro
        130                 135                 140

Ile Glu Arg Glu Ser Ser Ser Pro Leu Ser Ser Asn Gln Ser Glu Pro
145                 150                 155                 160

Gly Ser Ile Ala Leu Asn Ser Tyr His Ser Arg Asn Cys Ser Glu Ser
                165                 170                 175

Asp His Ser Arg Asn Gly Phe Asp Thr Asp Ser Ser Cys Leu Glu Ser
            180                 185                 190

His Ser Ser Leu Ser Asp Ser Glu Phe Pro Pro Asn Asn Lys Gly Glu
        195                 200                 205

Ile Lys Thr Glu Gly Gln Glu Leu Ile Thr Val Ile Lys Ala Pro Thr
    210                 215                 220

Ser Phe Gly Tyr Asp Lys Pro His Val Leu Val Asp Leu Leu Val Asp
225                 230                 235                 240

Asp Ser Gly Lys Glu Ser Leu Ile Gly Tyr Arg Pro Thr Glu Asp Ser
                245                 250                 255

Lys Glu Phe Ser
            260

<210> SEQ ID NO 81
<211> LENGTH: 260
<212> TYPE: PRT
<213> ORGANISM: Pongo abeli

<400> SEQUENCE: 81

Lys Ser Lys Glu Val Cys Ile Thr Ile Phe Asn Ser Ser Ile Lys Ser
1               5                   10                  15

Ser Leu Trp Ile Pro Val Val Ala Ala Leu Leu Leu Ile Leu Val Leu
            20                  25                  30

Ser Leu Val Phe Ile Cys Phe Tyr Ile Lys Lys Ile Asn Pro Leu Lys
        35                  40                  45

Glu Lys Ser Ile Ile Leu Pro Lys Ser Leu Ile Ser Val Val Arg Ser
    50                  55                  60

Ala Thr Leu Glu Thr Lys Pro Glu Ser Lys Tyr Val Ser Leu Ile Thr
65                  70                  75                  80

Ser Tyr Gln Pro Ser Ser Leu Glu Lys Glu Val Val Cys Glu Gly Pro
                85                  90                  95

Leu Ser Pro Ala Thr Val Pro Gly Met His Thr Glu Asp Asn Pro Gly
            100                 105                 110

Lys Val Glu His Thr Glu Glu Leu Ser Ser Ile Thr Glu Val Val Thr
        115                 120                 125

Thr Glu Glu Asn Ile Pro Asp Met Ala Pro Gly Ser His Leu Thr Pro
    130                 135                 140

Val Glu Arg Glu Ser Ser Ser Pro Leu Ser Ser Asn Gln Ser Glu Pro
145                 150                 155                 160

Cys Ser Ile Ala Leu Asn Ser Tyr His Ser Arg Asn Cys Ser Asp Ser
                165                 170                 175

Asp His Ser Arg Asn Gly Phe Asp Thr Asp Ser Ser Cys Leu Glu Ser
            180                 185                 190

His Ser Ser Leu Ser Asp Ser Glu Phe Pro Pro Ser Asn Lys Gly Glu
        195                 200                 205

Ile Lys Thr Glu Gly Gln Glu Leu Ile Thr Val Ile Lys Ala Pro Thr
    210                 215                 220

Ser Phe Gly Tyr Asp Lys Pro His Val Leu Val Asp Leu Leu Val Asp
```

```
                225                 230                 235                 240
Asp Ser Gly Lys Glu Ser Leu Ile Gly Tyr Arg Pro Thr Glu Asp Ser
                245                 250                 255
Lys Glu Phe Ser
            260

<210> SEQ ID NO 82
<211> LENGTH: 241
<212> TYPE: PRT
<213> ORGANISM: Bos taurus

<400> SEQUENCE: 82

Lys Ser Asp Glu Leu Cys Ile Thr Phe Ser Asp Asn Asn Thr Glu
1               5                   10                  15

Asp Pro Val Trp Ile Pro Ile Val Ala Ala Leu Leu Leu Phe Leu Val
                20                  25                  30

Phe Ala Leu Val Val Val Cys Cys Ile Ile Lys Lys Phe Tyr Pro Ile
                35                  40                  45

Lys Arg Glu Gly Thr Lys Leu Pro Lys Ser Leu Leu Ser Val Val Lys
            50                  55                  60

Asn Ala Ser Ser Glu Ala Lys Phe Asp Ser Lys Ile Ile Ser Pro Ile
65                  70                  75                  80

Thr Tyr Gln Pro Ile Ala Val Glu Asn Glu Gln Leu Ser Pro Gly Thr
                85                  90                  95

Ile Ser Ser Leu His Thr Glu Asp Asn Pro Gly Lys Val Glu His Gly
                100                 105                 110

Asp Leu Ser Ser Glu Met Glu Val Val Thr Ile Glu Glu Asn Ile Ser
            115                 120                 125

Asp Leu Ala Pro Cys Ser Pro Leu Thr Pro Gly Arg Glu Asp Ser Ile
130                 135                 140

His Ala Ser Ser Asn Gln Ser Glu Ser Cys Ser Ile Thr Leu Asn Ala
145                 150                 155                 160

Tyr His Ser Arg Asn Gly Ser Asp Ser Gly Leu Ala Val Ser Asp Asn
                165                 170                 175

Cys Ser Ser Ser Glu Phe Pro Pro Ser Asn Lys Thr Glu Val Lys Thr
                180                 185                 190

Glu Gly Gln Asp Phe Ile Thr Leu Arg Asn Thr Thr Thr Ser Phe Gly
            195                 200                 205

Tyr Asp Lys Pro His Val Leu Val Asp Leu Leu Val Asp Glu Gly Gly
210                 215                 220

Lys Glu Ser Leu Ile Gly Tyr Arg Leu Thr Ala Asp Ser Arg Glu Phe
225                 230                 235                 240

Ser

<210> SEQ ID NO 83
<211> LENGTH: 241
<212> TYPE: PRT
<213> ORGANISM: Cervus elaphus

<400> SEQUENCE: 83

Lys Ser Glu Glu Leu Cys Ile Thr Phe Ser Asp Ser Asn Thr Glu
1               5                   10                  15

Asp Pro Val Trp Ile Pro Ile Val Ala Ala Leu Val Leu Phe Leu Val
                20                  25                  30

Phe Ala Leu Val Val Ala Cys Cys Ile Phe Lys Lys Leu Asn Pro Ile
                35                  40                  45
```

Lys Pro Glu Gly Thr Lys Leu Pro Lys Ser Leu Leu Ser Val Val Lys
            50                  55                  60

Asn Ala Ser Ser Glu Ala Arg Leu Asp Ser Lys Val Ile Ser Pro Ile
 65                  70                  75                  80

Thr Tyr Gln Pro Ile Thr Val Glu Asn Glu Gln Leu Ser Pro Gly Thr
                85                  90                  95

Ile Ser Ser Val His Thr Glu Asp Pro Gly Lys Val Glu His Gly
            100                 105                 110

Asp Leu Ser Ser Glu Val Glu Val Thr Ile Glu Glu Asn Ile Ser
            115                 120                 125

Asp Leu Val Pro Cys Ser Pro Leu Thr Pro Glu Arg Glu Gly Ser Ile
130                 135                 140

His Ala Asn Ser Ser Gln Ser Glu Pro Cys Ser Ile Thr Leu Asn Ala
145                 150                 155                 160

Tyr His Ser Arg Asn Gly Ser Asp Ser Gly Leu Val Val Ser Asp Asn
                165                 170                 175

Cys Ser Ser Glu Phe Pro Pro Ser Asn Lys Thr Glu Val Lys Thr
            180                 185                 190

Glu Gly Gln Asp Phe Leu Thr Leu Arg Asn Thr Thr Ser Phe Gly
            195                 200                 205

Tyr Asp Lys Pro His Val Leu Val Asp Leu Leu Val Asp Glu Gly Gly
210                 215                 220

Lys Glu Ser Leu Ile Gly Tyr Arg Leu Thr Ala Asp Ser Arg Glu Phe
225                 230                 235                 240

Ser

<210> SEQ ID NO 84
<211> LENGTH: 244
<212> TYPE: PRT
<213> ORGANISM: Ailuropoda melanoleuca

<400> SEQUENCE: 84

Met Ser Lys Glu Leu Cys Ile Thr Thr Ser Asp Asp Arg Arg Met Asp
  1               5                  10                  15

Ser Val Trp Ile Pro Ile Val Ala Val Leu Phe Leu Val Leu Met
                 20                  25                  30

Leu Val Phe Val Phe Cys Tyr Thr Lys Lys Met Asn Pro Cys Lys Arg
             35                  40                  45

Glu Ser Ile Met Leu Pro Lys Ser Leu Leu Ser Val Val Lys Asn Ala
 50                  55                  60

Ser Ser Glu Thr Lys Ser Glu Ser Lys Cys Ile Ser Pro Ile Thr Tyr
 65                  70                  75                  80

Gln Pro Ile Val Pro Glu Asn Glu Lys Met Val Trp Glu Glu Gln Leu
                 85                  90                  95

Ser Pro Ala Thr Val Ala Gly Thr Pro Asn Glu Asp Asn Leu Gly Lys
            100                 105                 110

Met Glu His Arg Glu Asp Val Ser Ser Glu Ile Glu Val Val Thr Ile
            115                 120                 125

Glu Glu Asn Thr Ser Asp Met Ala Leu Gly Ser Pro Leu Asn Pro Gly
130                 135                 140

Met Arg Glu Asn Ser Val His Ser Ser Asn Gln Ser Glu Pro Cys
145                 150                 155                 160

Val Val Ala Phe Asn Ser Tyr His Ser Arg Asn Gly Ser Asp Ser Gly
                165                 170                 175

```
Val Val Glu Ser Asp Gly Phe Leu Ser Asp Ser Glu Phe Pro Pro Asn
            180                 185                 190

Asn Lys Thr Glu Met Lys Pro Glu Val Gln Glu Cys Val Val Leu Arg
            195                 200                 205

Asn Thr Ile Thr Ser Phe Gly Tyr Asp Lys Pro His Val Leu Val Asp
            210                 215                 220

Leu Pro Val Gly Glu Gly Gly Lys Glu Ser Leu Ile Gly Tyr Arg Leu
225                 230                 235                 240

Thr Ala Asp Ser

<210> SEQ ID NO 85
<211> LENGTH: 240
<212> TYPE: PRT
<213> ORGANISM: Mus musculus

<400> SEQUENCE: 85

Lys Ser Lys Asp Val Cys Ile Pro Pro Phe His Asp Asp Arg Lys Asp
1               5                   10                  15

Ser Ile Trp Ile Leu Val Val Ala Pro Leu Thr Val Phe Thr Val Val
            20                  25                  30

Ile Leu Val Phe Ala Tyr Trp Tyr Thr Lys Lys Asn Ser Phe Lys Arg
        35                  40                  45

Lys Ser Ile Met Leu Pro Lys Ser Leu Leu Ser Val Val Lys Ser Ala
    50                  55                  60

Thr Leu Glu Thr Lys Pro Glu Ser Lys Tyr Ser Leu Val Thr Pro His
65                  70                  75                  80

Gln Pro Ala Val Leu Glu Ser Glu Thr Val Ile Cys Glu Glu Pro Leu
                85                  90                  95

Ser Thr Val Thr Ala Pro Asp Ser Pro Glu Ala Ala Glu Gln Glu Glu
            100                 105                 110

Leu Ser Lys Glu Thr Lys Ala Leu Glu Ala Gly Gly Ser Thr Ser Ala
        115                 120                 125

Met Thr Pro Asp Ser Pro Pro Thr Pro Thr Gln Arg Arg Ser Phe Ser
    130                 135                 140

Leu Leu Ser Ser Asn Gln Ser Gly Pro Cys Ser Leu Thr Ala Tyr His
145                 150                 155                 160

Ser Arg Asn Gly Ser Asp Ser Gly Leu Val Gly Ser Gly Ser Ser Ile
                165                 170                 175

Ser Asp Leu Glu Ser Leu Pro Asn Asn Asn Ser Glu Thr Lys Met Ala
            180                 185                 190

Glu His Asp Pro Pro Pro Val Arg Lys Ala Pro Met Ala Ser Gly Tyr
        195                 200                 205

Asp Lys Pro His Met Leu Val Asp Val Leu Val Asp Val Gly Gly Lys
    210                 215                 220

Glu Ser Leu Met Gly Tyr Arg Leu Thr Gly Glu Ala Gln Glu Leu Ser
225                 230                 235                 240

<210> SEQ ID NO 86
<211> LENGTH: 240
<212> TYPE: PRT
<213> ORGANISM: Rattus norvegicus

<400> SEQUENCE: 86

Thr Ser Lys Asp Ala Cys Ile Pro Phe Leu His Asp Asp Arg Glu Glu
1               5                   10                  15
```

```
Ser Ile Trp Met Leu Leu Val Ala Pro Leu Leu Phe Leu Thr Ile Val
             20                  25                  30

Val Pro Ala Leu Val Cys Cys Tyr Ile Lys Lys Asn Pro Phe Lys Arg
         35                  40                  45

Lys Ser Ile Met Leu Pro Lys Ser Leu Leu Ser Val Val Lys Asn Ala
 50                  55                  60

Thr Ser Glu Thr Lys Pro Glu Ser Lys Tyr Ser Leu Val Thr Ser Cys
 65                  70                  75                  80

Gln Pro Ala Val Leu Glu Asn Glu Thr Val Ile Cys Glu Glu His Leu
                 85                  90                  95

Ser Thr Val Thr Thr Pro Asp Ser Leu Glu Ala Pro Gln Glu Glu
                100                 105                 110

Leu Ser Lys Gly Thr Val Ala Thr Val Ala Glu Gly Asn Thr Ser Pro
            115                 120                 125

Glu Thr Thr Asp Ser Pro Leu Thr Pro Val Gln Ser Gly His Phe Ser
130                 135                 140

Leu Ser Ser Ser Asn Gln Ser Gly Ser Cys Ser Leu Thr Thr Tyr His
145                 150                 155                 160

Ser Arg Asp Gly Ser Asp Ser Gly Leu Val Gly Thr Gly Ser Ser Ile
                165                 170                 175

Ser Asp Ser Asp Phe Leu Pro Asn Asn Asp Ser Glu Thr Lys Met Ala
            180                 185                 190

Asp Pro Ala Pro Thr Pro Val Arg Lys Ala Leu Thr Phe Ser Gly Tyr
        195                 200                 205

Asp Lys Pro His Val Leu Val Asp Val Pro Val Asp Gly Glu Gly Lys
    210                 215                 220

Glu Ser Leu Ile Gly Tyr Arg Leu Thr Gly Asp Thr Gln Glu Leu Ser
225                 230                 235                 240

<210> SEQ ID NO 87
<211> LENGTH: 117
<212> TYPE: PRT
<213> ORGANISM: Homo sapiens

<400> SEQUENCE: 87

Ser Asn Ile Phe Arg Val Gly His Leu Ser Asn Ile Ser Cys Tyr Glu
1               5                  10                  15

Thr Met Ala Asp Ala Ser Thr Glu Leu Gln Gln Val Ile Leu Ile Ser
             20                  25                  30

Val Gly Thr Phe Ser Leu Leu Ser Val Leu Ala Gly Ala Cys Phe Phe
         35                  40                  45

Leu Val Leu Lys Tyr Arg Gly Leu Ile Lys Tyr Trp Phe His Thr Pro
 50                  55                  60

Pro Ser Ile Pro Leu Gln Ile Glu Glu Tyr Leu Lys Asp Pro Thr Gln
 65                  70                  75                  80

Pro Ile Leu Glu Ala Leu Asp Lys Asp Ser Ser Pro Lys Asp Asp Val
                 85                  90                  95

Trp Asp Ser Val Ser Ile Ile Ser Phe Pro Glu Lys Glu Gln Glu Asp
                100                 105                 110

Val Leu Gln Thr Leu
            115

<210> SEQ ID NO 88
<211> LENGTH: 117
<212> TYPE: PRT
<213> ORGANISM: Papio anubis
```

<400> SEQUENCE: 88

```
Ser Asn Ile Phe Arg Leu Gly His Leu Ser Asn Thr Ser Cys Tyr Glu
1               5                   10                  15

Thr Met Ala Asp Ala Ser Thr Glu Leu Gln Gln Val Ile Leu Ile Ser
            20                  25                  30

Val Gly Thr Phe Ser Leu Leu Ser Val Leu Ala Gly Ala Cys Cys Phe
        35                  40                  45

Leu Val Leu Lys Tyr Arg Gly Leu Ile Lys Tyr Trp Phe His Thr Pro
50                  55                  60

Pro Ser Ile Pro Leu Gln Ile Glu Glu Tyr Leu Lys Asp Pro Thr Gln
65                  70                  75                  80

Pro Ile Leu Glu Val Leu Asp Lys Asp Ser Ser Pro Lys Asp Asp Val
                85                  90                  95

Trp Asp Ser Val Ser Ile Ile Ser Phe Pro Glu Lys Glu Gln Glu Asp
                100                 105                 110

Val Leu Gln Thr Leu
            115
```

<210> SEQ ID NO 89
<211> LENGTH: 115
<212> TYPE: PRT
<213> ORGANISM: Callicebus moloch

<400> SEQUENCE: 89

```
Ser Asn Val Asn Gly His Leu Ser Asn Thr Ser Cys Tyr Lys Ile Met
1               5                   10                  15

Glu Asp Ala Ser Thr Lys Leu Gln Gln Val Ile Leu Ile Ser Val Gly
            20                  25                  30

Thr Phe Ser Leu Met Ser Val Leu Ala Gly Ala Cys Phe Phe Leu Val
        35                  40                  45

Leu Lys Tyr Arg Gly Leu Ile Lys Tyr Trp Phe His Thr Pro Pro Ser
50                  55                  60

Ile Pro Leu Gln Ile Glu Glu Tyr Leu Lys Asp Pro Ala Gln Pro Ile
65                  70                  75                  80

Leu Glu Ala Leu Asp Lys Asp Ser Ser Pro Lys Asp Asp Val Trp Asp
                85                  90                  95

Ser Val Ser Ile Ile Ser Leu Pro Glu Lys Gly Gln Glu Asp Val Leu
                100                 105                 110

Gln Thr His
        115
```

<210> SEQ ID NO 90
<211> LENGTH: 115
<212> TYPE: PRT
<213> ORGANISM: Cervus elaphus
<220> FEATURE:
<221> NAME/KEY: misc_feature
<222> LOCATION: (15)..(15)
<223> OTHER INFORMATION: Xaa can be any naturally occurring amino acid
<220> FEATURE:
<221> NAME/KEY: misc_feature
<222> LOCATION: (40)..(40)
<223> OTHER INFORMATION: Xaa can be any naturally occurring amino acid

<400> SEQUENCE: 90

```
Glu Asn Val Ser Arg Pro Gly His Leu Ser Asn Ile Ser Cys Xaa Glu
1               5                   10                  15

Thr Ala Ala Asp Ala Ser Val Lys Leu Gln Gln Asp Ile Leu Ala Ala
```

```
            20                  25                  30
Ala Thr Thr Phe Leu Val Leu Xaa Val Val Gly Ser Cys Leu Phe
            35                  40                  45
Leu Val Leu Lys Tyr Arg Gly Leu Val Lys His Trp Phe His Ser Pro
        50                  55                  60
Pro Ser Ile Pro Ser Gln Ile Glu Glu Tyr Leu Lys Asp Pro Asp Gln
 65                  70                  75                  80
Pro Ile Leu Asp Ala Leu Asp Lys Asp Ser Ser Pro Lys Asp Asp Ala
                85                  90                  95
Trp Asp Ser Val Ser Ile Val Thr Phe Pro Glu Asn Glu Gln Glu Gly
                100                 105                 110
Ser Pro Gln
        115

<210> SEQ ID NO 91
<211> LENGTH: 134
<212> TYPE: PRT
<213> ORGANISM: Bos tauras

<400> SEQUENCE: 91

Glu Asn Ile Ser Arg Pro Gly His Leu Ser Asn Ile Ser Cys Cys Glu
 1               5                  10                  15
Thr Ala Ala Asp Ala Ser Val Lys Leu Gln Gln Asp Phe Leu Ala Ala
                20                  25                  30
Gly Thr Thr Phe Leu Val Leu Ser Val Val Gly Ser Cys Leu Phe
            35                  40                  45
Leu Val Leu Arg Tyr Arg Gly Leu Val Lys His Trp Phe His Ser Pro
        50                  55                  60
Pro Ser Ile Pro Ser Gln Ile Glu Glu Tyr Leu Lys Asp Pro Ala Gln
 65                  70                  75                  80
Pro Ile Leu Asp Ala Leu Asp Lys Asp Ser Ser Pro Lys Asp Asp Thr
                85                  90                  95
Trp Asp Ser Val Ser Val Val Thr Phe Pro Glu Asn Glu Gln Glu Gly
                100                 105                 110
Ser Pro Gln Ser Thr Leu Asn Gln Ser Ala Gly Pro Ser His Gln Pro
            115                 120                 125
Thr Glu Gly Val Leu Cys
        130

<210> SEQ ID NO 92
<211> LENGTH: 145
<212> TYPE: PRT
<213> ORGANISM: Sus scrofa

<400> SEQUENCE: 92

Glu Asn Ile Ser Arg Ser Gly His Leu Ser Asn Ile Ser Cys Ser Glu
 1               5                  10                  15
Thr Thr Ala Asp Ala Ser Thr Lys Leu Gln Gln Val Ile Leu Ile Ala
                20                  25                  30
Val Gly Thr Phe Leu Leu Leu Val Val Gly Ala Cys Leu Phe
            35                  40                  45
Leu Val Leu Lys Phe Arg Gly Leu Val Lys Tyr Trp Phe His Ser Pro
        50                  55                  60
Pro Arg Ile Pro Val Gln Ile Glu Glu Tyr Leu Lys Asp Pro Ala Gln
 65                  70                  75                  80
Pro Ile Leu Asp Ala Leu Asp Lys Asp Ser Ser Ser Arg Asp Asp Ala
```

```
                    85                  90                  95

Trp Asp Ser Val Ser Ile Val Ser Phe Pro Glu Asn His Arg Glu Asp
                100                 105                 110

Thr Leu Gln Ser Thr Leu Thr Gln Ser Thr Val Ser Ser His Lys Pro
            115                 120                 125

Met Asp Gly Ala Pro Ser Ala Asn Thr Ala Ala Asp Val Ser Val Pro
    130                 135                 140

Val
145

<210> SEQ ID NO 93
<211> LENGTH: 111
<212> TYPE: PRT
<213> ORGANISM: Ailuropoda melanoleuca

<400> SEQUENCE: 93

Tyr Asn Ile Ser Arg Pro Gly His Leu Ser Asn Val Ser Cys Tyr Glu
1               5                   10                  15

Thr Thr Met Asp Ala Thr Thr Lys Leu Gln Gln Val Ile Val Ile Ala
            20                  25                  30

Val Gly Val Phe Leu Ser Leu Leu Ala Leu Ala Gly Ala Cys Phe Phe
        35                  40                  45

Leu Val Leu Arg Tyr Lys Gly Leu Val Lys Tyr Trp Phe His Ser Pro
    50                  55                  60

Pro Ser Ile Pro Ser Gln Ile Glu Glu Tyr Leu Lys Asp Pro Ser Gln
65                  70                  75                  80

Pro Ile Leu Glu Ala Leu Asp Lys Asp Thr Ser Pro Thr Asp Asp Ala
                85                  90                  95

Trp Asp Ser Val Ser Val Ile Ser Phe Ala Glu Lys Asp Arg Glu
                100                 105                 110

<210> SEQ ID NO 94
<211> LENGTH: 117
<212> TYPE: PRT
<213> ORGANISM: Mus sp.

<400> SEQUENCE: 94

Lys Lys Ile Arg Pro His Gly Leu Leu Ser Asn Val Ser Cys His Glu
1               5                   10                  15

Thr Thr Ala Asn Ala Ser Ala Arg Leu Gln Gln Val Ile Leu Ile Pro
            20                  25                  30

Leu Gly Ile Phe Ala Leu Leu Leu Gly Leu Thr Gly Ala Cys Phe Thr
        35                  40                  45

Leu Phe Leu Lys Tyr Gln Ser Arg Val Lys Tyr Trp Phe Gln Ala Pro
    50                  55                  60

Pro Asn Ile Pro Glu Gln Ile Glu Glu Tyr Leu Lys Asp Pro Asp Gln
65                  70                  75                  80

Phe Ile Leu Glu Val Leu Asp Lys Asp Gly Ser Pro Lys Glu Asp Ser
                85                  90                  95

Trp Asp Ser Val Ser Ile Ile Ser Ser Pro Glu Lys Glu Arg Asp Asp
                100                 105                 110

Val Leu Gln Thr Pro
        115

<210> SEQ ID NO 95
<211> LENGTH: 128
<212> TYPE: PRT
```

<213> ORGANISM: Gallus gallus

<400> SEQUENCE: 95

Ser Arg Phe His Leu Ile Gly Leu Gln Thr Val Pro Glu Cys Tyr Arg
1               5                   10                  15

Thr Thr Ile Ser Glu Ala Thr Lys Ala Gly Tyr Ile Val Ala Ile Phe
            20                  25                  30

Met Ser Val Gly Leu Leu Leu Ile Val Ile Val Gly Phe Phe Cys
        35                  40                  45

Leu Trp Arg Asn Gln Lys Ala Ile Lys Tyr Leu Ser Gln Pro Pro Leu
    50                  55                  60

Arg Ile Pro Ser His Phe Glu Glu Tyr Leu Arg Asp Pro Ser Met Pro
65                  70                  75                  80

Gln Leu Glu Val Leu Glu Asn His Asp Glu Asp Pro Gln Asp Leu Leu
                85                  90                  95

Thr Val Val Tyr Thr Gly Glu Gly Ser Ser Ala Tyr Gly Asp Met Leu
            100                 105                 110

Asp Gly Asn Thr Cys Ser His Ser Ser Ser Ser Arg Asp Val Thr
        115                 120                 125

<210> SEQ ID NO 96
<211> LENGTH: 106
<212> TYPE: PRT
<213> ORGANISM: Xenopus laevis

<400> SEQUENCE: 96

Val Ile Pro Asp Leu Thr Gly Glu Thr Ser His Val Val Cys Ala Lys
1               5                   10                  15

Thr Pro Gly Ala Pro Gly Val Thr Ala Asp Lys Val Ile Phe Ile Ser
            20                  25                  30

Val Gly Leu Ile Ile Leu Cys Cys Ile Phe Leu Gly Phe Ser Tyr Ala
        35                  40                  45

Phe Ser Arg His Arg Gly Arg Ile Lys Thr Trp Leu Tyr Pro Pro Tyr
    50                  55                  60

Asn Ile Pro Pro Asp Ile Glu Gln Tyr Leu Gln Glu Pro Pro Trp Asn
65                  70                  75                  80

Gly His Leu Glu Lys Ser Lys Glu Leu His Ser Ala Glu Gln Tyr
                85                  90                  95

Asp Ile Ile Ser Ile Val Glu Ser Glu Ser
            100                 105

<210> SEQ ID NO 97
<211> LENGTH: 93
<212> TYPE: PRT
<213> ORGANISM: Homo sapiens

<400> SEQUENCE: 97

Met Val Cys Leu Ala Leu Leu Gly Cys Phe Ala Leu Leu Trp Cys Val
1               5                   10                  15

Tyr Lys Lys Thr Lys Tyr Ala Phe Ser Pro Arg Asn Ser Leu Pro Gln
            20                  25                  30

His Leu Lys Glu Phe Leu Gly His Pro His Asn Thr Leu Leu Phe
        35                  40                  45

Phe Ser Phe Pro Leu Ser Asp Glu Asn Asp Val Phe Asp Lys Leu Ser
    50                  55                  60

Val Ile Ala Glu Asp Ser Glu Ser Gly Lys Gln Asn Pro Gly Asp Ser
65                  70                  75                  80

```
Cys Ser Leu Gly Thr Pro Pro Gly Gln Gly Pro Gln Ser
                85                  90

<210> SEQ ID NO 98
<211> LENGTH: 93
<212> TYPE: PRT
<213> ORGANISM: Papio anubis

<400> SEQUENCE: 98

Val Val Cys Leu Ala Leu Leu Gly Cys Phe Ala Leu Leu Trp Cys Ile
1               5                   10                  15

Tyr Lys Lys Thr Lys Tyr Thr Phe Ser Pro Gly Asn Ser Leu Pro Gln
            20                  25                  30

His Leu Lys Glu Phe Leu Gly His Pro His His Asn Thr Leu Leu Phe
        35                  40                  45

Phe Ser Phe Pro Phe Ser Asp Glu Asn Asp Val Phe Asp Lys Leu Ser
    50                  55                  60

Val Ile Ala Glu Asp Ser Glu Ser Ser Lys Gln Asn Pro Asp Asp Ser
65                  70                  75                  80

Cys Ser Leu Gly Thr Pro Pro Gly Gln Gly Pro Gln Ser
                85                  90

<210> SEQ ID NO 99
<211> LENGTH: 93
<212> TYPE: PRT
<213> ORGANISM: Callithrix jacchus

<400> SEQUENCE: 99

Val Val Cys Leu Ala Leu Leu Gly Cys Phe Thr Leu Leu Trp Tyr Ile
1               5                   10                  15

Tyr Lys Lys Thr Lys Tyr Ala Phe Cys Pro Gly Asn Ser Leu Pro Gln
            20                  25                  30

His Leu Lys Glu Phe Leu Gly His Pro His His Asn Thr Leu Leu Phe
        35                  40                  45

Leu Ser Phe Pro Phe Ser Asp Glu Asn Asp Val Phe Asp Lys Leu Ser
    50                  55                  60

Val Ile Thr Glu Asp Ser Glu Ser Gly Lys Gln Asn Pro Gly Asp Gly
65                  70                  75                  80

Arg Ser Leu Arg Thr Leu Pro Gly Gln Gly Ser Gln Ser
                85                  90

<210> SEQ ID NO 100
<211> LENGTH: 91
<212> TYPE: PRT
<213> ORGANISM: Otolemur garnetti

<400> SEQUENCE: 100

Val Ala Val Leu Leu Leu Gly Cys Phe Ala Leu Leu Trp Cys Ile
1               5                   10                  15

Tyr Lys Lys Thr Lys Tyr Ala Phe Ser Pro Gly Asn Ser Leu Pro Gln
            20                  25                  30

His Leu Lys Glu Phe Leu Gly His Pro His His Ser Thr Leu Leu Phe
        35                  40                  45

Phe Ser Phe Pro Leu Ser Asp Glu Asn Glu Val Phe Asp Lys Leu Ser
    50                  55                  60

Val Ile Ile Glu Asp Ser Glu Ser Lys Gln Asn Ala Ser Asp Ser
65                  70                  75                  80
```

Cys Ser Phe Arg Thr Leu Ser Glu Glu Gly Pro
                85                  90

<210> SEQ ID NO 101
<211> LENGTH: 91
<212> TYPE: PRT
<213> ORGANISM: Oryctolagus cuniculus

<400> SEQUENCE: 101

Val Val Phe Leu Val Leu Leu Ala Cys Phe Ala Leu Leu Trp Cys Ile
1               5                   10                  15

Tyr Lys Lys Thr Lys Tyr Thr Phe Ser Pro Gly Asn Ala Leu Pro Gln
                20                  25                  30

His Leu Lys Glu Phe Leu Gly Asn Pro His His Gly Thr Arg Leu Phe
            35                  40                  45

Phe Ser Phe Pro Leu Leu Asp Glu Asn Glu Val Phe Asp Lys Leu Ser
        50                  55                  60

Val Val Ala Glu Asp Ser Glu Gly Ser Lys Gln Ser Pro Gly Glu Ser
65                  70                  75                  80

Cys Gly Leu Gly Thr Leu Ser Gly Gln Glu Pro
                85                  90

<210> SEQ ID NO 102
<211> LENGTH: 120
<212> TYPE: PRT
<213> ORGANISM: Sus scrofa

<400> SEQUENCE: 102

Ala Ala Phe Leu Leu Leu Leu Gly Cys Phe Ile Leu Leu Arg Cys Ile
1               5                   10                  15

Tyr Lys Lys Thr Lys Asn Ala Phe Pro Pro Arg Asn Ser Leu Pro Gln
                20                  25                  30

His Leu Lys Glu Phe Leu Ser His Pro His His Ser Thr Leu Leu Leu
            35                  40                  45

Phe Ser Ile Pro Leu Ser Asp Glu Asn Glu Val Phe Asp Lys Leu Ser
        50                  55                  60

Val Ile Thr Asp Ala Ser Glu Ser His Lys Gln Asn Ser Gly Ala Gly
65                  70                  75                  80

Cys Ser Leu Gly Ala Gln Cys Gly Gln Gly Ser Phe Glu Leu Val Ser
                85                  90                  95

Gln Glu Gly Thr Pro Ser Ala Glu Cys Ser Asp Pro Phe Leu Leu Thr
                100                 105                 110

Ser Ala Ser Glu Asp Asp Gln Arg
            115                 120

<210> SEQ ID NO 103
<211> LENGTH: 119
<212> TYPE: PRT
<213> ORGANISM: Canis familiaris

<400> SEQUENCE: 103

Val Ala Leu Leu Leu Leu Gly Cys Ser Ala Leu Leu Trp Cys Leu Tyr
1               5                   10                  15

Lys Arg Thr Lys His Val Phe Ser Pro Arg Asn Cys Leu Pro Gln His
                20                  25                  30

Leu Lys Glu Phe Leu Gly His Pro His His Asn Thr Leu Leu Phe Phe
            35                  40                  45

Ser Phe Pro Pro Ser Asp Glu Asn Glu Val Phe Asp Lys Leu Ser Val

```
                     50                  55                  60
Ile Thr Gln Val Ser Glu Ser Ser Arg Gln Ser Ser Gly Asn Ser Cys
 65                  70                  75                  80

Thr Pro Gly Thr Pro Ser Gly Gln Gly Ser Ser Glu Leu Val Pro Lys
                 85                  90                  95

Glu Gly Ala Asn Thr Gln Gly Cys Ser Thr Pro Leu Leu Leu Ser Pro
            100                 105                 110

Ala Thr Glu Gly His Gln Ser
            115

<210> SEQ ID NO 104
<211> LENGTH: 117
<212> TYPE: PRT
<213> ORGANISM: Mus musculus

<400> SEQUENCE: 104

Val Val Phe Leu Phe Leu Leu Gly Cys Phe Val Val Leu Trp Leu Ile
 1               5                  10                  15

Tyr Lys Lys Thr Lys His Thr Phe Arg Ser Gly Thr Ser Leu Pro Gln
                 20                  25                  30

His Leu Lys Glu Phe Leu Gly His Pro His His Ser Thr Phe Leu Leu
             35                  40                  45

Phe Ser Phe Pro Pro Pro Glu Glu Ala Glu Val Phe Asp Lys Leu Ser
 50                  55                  60

Ile Ile Ser Glu Glu Ser Gly Ser Lys Gln Ser Pro Glu Asp Asn
 65                  70                  75                  80

Cys Ala Ser Glu Pro Pro Ser Asp Pro Gly Pro Arg Glu Leu Glu Ser
                 85                  90                  95

Lys Asp Glu Ala Pro Ser Pro His Asp Asp Pro Lys Leu Leu Thr
            100                 105                 110

Ser Thr Ser Glu Val
            115

<210> SEQ ID NO 105
<211> LENGTH: 115
<212> TYPE: PRT
<213> ORGANISM: Gallus gallus

<400> SEQUENCE: 105

Ala Val Ile Ile Ser Val Pro Val Cys Phe Ser Phe Trp Tyr Leu
 1               5                  10                  15

Tyr Arg Phe Thr Lys His Val Phe Phe Pro Ser Tyr Ile Phe Pro Gln
                 20                  25                  30

His Leu Lys Glu Phe Leu Ser Lys Pro Pro Ser Gly Ser Gln Phe Phe
             35                  40                  45

Ser Pro Val Pro Gln Glu Glu His Gln Phe His Asp Trp Leu Thr Val
 50                  55                  60

Ile Ser Glu Glu Pro Lys Ser Gln Arg Asp Glu Thr Val Glu Glu Ala
 65                  70                  75                  80

Ser Lys Thr Ala Glu His His Gln Asp Ser Lys Gln Glu Ile Ser Asp
                 85                  90                  95

Ser Glu Ile Leu Pro Pro Leu Glu Arg Asp Gln Thr Leu Leu Thr Leu
            100                 105                 110

Gln Ser Gly
            115
```

-continued

```
<210> SEQ ID NO 106
<211> LENGTH: 73
<212> TYPE: PRT
<213> ORGANISM: Xenopus tropicalis

<400> SEQUENCE: 106

Leu Ser Ala Val Ile Val Val Gly Met Phe Tyr Leu Gly Ile Ser Ile
1               5                   10                  15

Tyr Lys Ala Ala Lys Tyr Leu Phe Phe Pro Lys Tyr Ser Phe Pro Glu
            20                  25                  30

His Leu Lys Glu Tyr Leu Ser Gln Pro Phe Tyr Ser Ser Pro His Leu
        35                  40                  45

Ser Thr Gln Gly Pro Asp Asp Val Ala Glu Pro Tyr Gly Thr Leu Thr
    50                  55                  60

Leu Val Ser Glu Glu Asn Pro Glu Val
65                  70

<210> SEQ ID NO 107
<211> LENGTH: 72
<212> TYPE: PRT
<213> ORGANISM: Xenopus laevis

<400> SEQUENCE: 107

Leu Ser Pro Val Ile Ile Val Gly Leu Phe Tyr Leu Gly Ser Arg Ile
1               5                   10                  15

Asn Lys Val Ala Lys Tyr Leu Phe Val Pro Lys Tyr Ser Phe Pro Glu
            20                  25                  30

His Leu Lys Glu Tyr Leu Ser Gln Pro Phe Tyr Ser Pro Pro His Leu
        35                  40                  45

Thr Gln Gly Pro Asp Asp Gly Gly Asp Pro Cys Gly Thr Leu Thr Leu
    50                  55                  60

Val Ser Glu Glu Asn Leu Glu Val
65                  70

<210> SEQ ID NO 108
<211> LENGTH: 4
<212> TYPE: PRT
<213> ORGANISM: Artificial Sequence
<220> FEATURE:
<223> OTHER INFORMATION: Synthetic

<400> SEQUENCE: 108

Arg Gln Ile Lys
1

<210> SEQ ID NO 109
<211> LENGTH: 4
<212> TYPE: PRT
<213> ORGANISM: Artificial Sequence
<220> FEATURE:
<223> OTHER INFORMATION: Synthetic

<400> SEQUENCE: 109

Lys Gln Ile Lys
1

<210> SEQ ID NO 110
<211> LENGTH: 22
<212> TYPE: PRT
<213> ORGANISM: Artificial Sequence
<220> FEATURE:
<223> OTHER INFORMATION: Synthetic
<220> FEATURE:
```

```
<221> NAME/KEY: misc_feature
<222> LOCATION: (13)..(13)
<223> OTHER INFORMATION: Xaa is norleucine.

<400> SEQUENCE: 110

Val Gln Arg Lys Ala Ile His Glu Leu Ile Gln Val Xaa Ala Glu Leu
1               5                   10                  15

Ser Pro Ala Ala Lys Thr
            20
```

PEPTIDE-BASED INHIBITOR OF INTERLEUKIN-10 OR INTERFERON-GAMMA SIGNALING

CROSS-REFERENCE TO RELATED APPLICATIONS

This patent application is the U.S. national phase of International Patent Application No. PCT/US2011/036010, filed May 11, 2011, which claims the benefit of U.S. Provisional Patent Application No. 61/333,512, filed May 11, 2010, each of which is incorporated by reference in its entirety herein.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 68,669 Byte ASCII (Text) file named "711382ST25.TXT," dated Oct. 18, 2012.

BACKGROUND OF THE INVENTION

Cytokine signaling by IL10 and IFN-gamma plays crucial roles in inflammation, cancer growth and autoimmune diseases. IFN-gamma, produced primarily by natural killer cells, is associated with anti-virus, pro-apoptotic tumor functions. However, recent studies have shown that aberrant IFN-gamma expression is associated with a number of autoimmune and auto-inflammatory diseases, liver cancers, papillomas, and breast cancers. In addition, IFN-gamma signaling on T cells is a critical step in initiating an adaptive immune response in graft-versus-host-disease (GVHD). GVHD remains one of the most prevalent causes of morbidity and mortality after bone marrow transplantations in leukemia patients.

IL10 is an anti-inflammatory cytokine and is involved in immune regulation and inflammation. It controls the immune response, preventing hosts from exaggerated inflammatory and immune reactions. However, it also disarms innate as well as adaptive responses, creating favorable conditions for the persistence of pathogens. Epstein-Barr virus, Orf virus, bovine papular stomatitis virus, lumpy skin disease virus and cytomegaloviruses encode variants of IL10 that allow them to escape eradication by immune system. In addition, several pathogens, like HIV-1, Dengue virus, influenza virus, measles virus, and West Nile virus are capable of stimulating IL10 production, which leads to impaired immune response. Thus, inhibition of IL10 activity may lead to a new way of treating infectious diseases, autoimmune diseases, and cancer. Blockade of IL10 was also suggested to be an effective adjuvant to specifically enhance CD4 T cell immunity and protection following vaccination.

Currently, there are no selective inhibitors of cytokines signaling, except antibodies. Thus, there remains a desire for selective inhibitors, particularly inhibitors of IFN-gamma and IL10 signaling.

BRIEF SUMMARY OF THE INVENTION

The invention provides an isolated or purified peptide or peptidomimetic comprising the amino acid sequence of any of SEQ ID NOs: 1-75 and 110 or inverse sequence thereof, wherein the peptide or peptidomimetic comprises about 35 or fewer amino acid residues. The invention also provides a nucleic acid encoding the peptide or peptidomimetic, a cell comprising the peptide or peptidomimetic or nucleic acid encoding same, an antibody that binds to the peptide or peptidomimetic, and a pharmaceutical composition comprising the peptide or peptidomimetic.

The invention further provides a method of inhibiting cytokine signaling or STAT protein activation in a cell comprising administering the peptide or peptidomimetic to the cell. In one aspect, the invention provides a method of inhibiting IL10 signaling or STAT3 activation in a cell comprising introducing into the cell a peptide or peptidomimetic comprising the amino acid sequence of any of SEQ ID NOs: 1-38 and 72-75, or inverse sequence thereof. The invention provides a method of treating or preventing a disease associated with IL10 signaling or STAT3 activation in a host, which method comprises administering a peptide or peptidomimetic comprising the amino acid sequence of any of SEQ ID NOs: 1-38 and 72-75, or inverse sequence thereof, to the host.

In another aspect, the invention provides a method of inhibiting IFN-gamma signaling or STAT1 activation in a cell comprising introducing into the cell a peptide or peptidomimetic comprising the amino acid sequence of any of SEQ ID NOs: 39-71 and 110, or inverse sequence thereof. In a related aspect, the invention provides a method of treating or preventing a disease associated with IFN-gamma signaling or STAT1 activation in a host, which method comprises administering a peptide or peptidomimetic comprising the amino acid sequence of any of SEQ ID NOs: 39-71 and 110, or inverse sequence thereof, to the host.

Related compounds, compositions, and methods also are provided, as will be apparent from the detailed description of the invention.

DETAILED DESCRIPTION OF THE INVENTION

Figure 1:
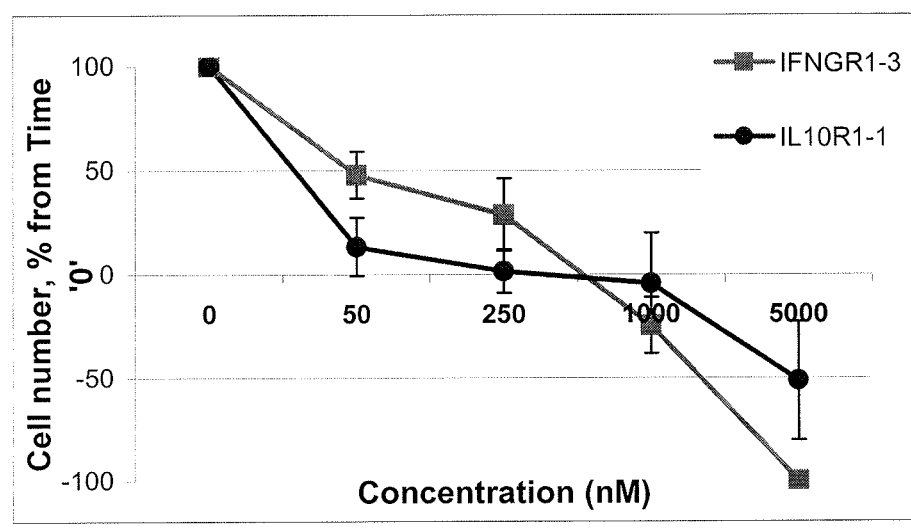
FIG. 1 is a graph of cell number plotted against concentration of peptide or peptidomimetic mimicking JAK1-binding sites of IL10R1 and IFNGR1. Cells were exposed to compounds for 48 hours and cell number was determined with the help of MTT assay.
Figure 2:
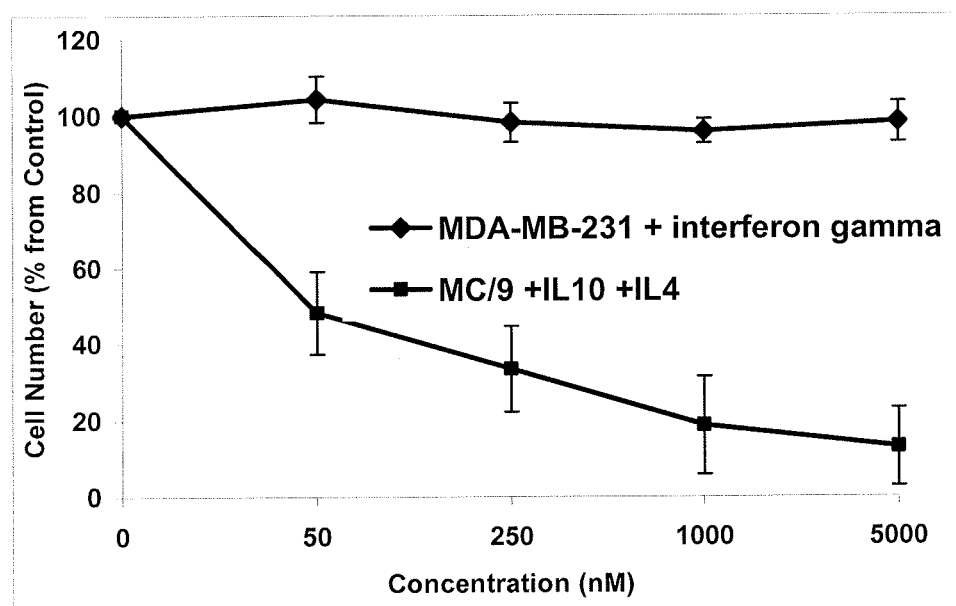
FIG. 2 is a graph of cell number plotted against concentration of IL10-HF-1, showing that the peptide or peptidomimetic inhibits IL10 dependent growth of mouse monocytes MC/9 with a $GI_{50}=50$ nM, but does not inhibit IFN-gamma-dependent growth of breast cancer cells MDA-MB-231. Cells were exposed to IL10-HF-1 for 48 hours and cell number was determined with the help of MTT assay.

The invention provides peptides and peptidomimetics comprising an amino acid sequence of any of SEQ ID NOs: 1-75 and 110, or the inverse sequences thereof. According to a preferred aspect of the invention, the peptides and polypeptides provided herein can inhibit cytokine signaling, such as by IFN-gamma or IL10, or activation of STAT proteins, especially STAT1 or STAT3 proteins.

Without wishing to be bound by any particular theory or mechanism of action, it is believed that both IL10 and IFN-gamma signal through heterodimeric receptors, and the peptides and peptidomimetic compounds provided herein interfere with the formation of the signaling complexes. Although many features of the signaling cascades still remain unclear, it is thought that the IFN-gamma receptor complex is composed of one IFN-gamma dimer, two IFN-gamma Receptor-1 (IFNGR1) chains, two IFN-gamma Receptor-2 (IFNGR2) chains, two Jak1 molecules, and two Jak2 molecules. IFNGR1 is pre-associated with Jak1 and IFNGR2 with Jak2. IFN-gamma binding to IFNGR leads to STAT1 phosphorylation and activation of transcription of genes containing the gamma activation sequence (GAS) in the promoter.

Similarly, the extracellular domain of the recombinant human IL10 receptor, when bound to IL10 forms a complex containing two IL10 homodimers and four receptor monomers. In addition, a single IL10 dimer could bind two receptors, similar to IFN-gamma. The topological similarity of IL10 to IFN-gamma may be a reflection of the close relationship between the biological effects of these two cytokines. IL10 Receptor-1 (IL10R1) also associates with Jak1 and IL10 Receptor-2 (IL10R2) associates with Tyk-2 kinase. IL10 binding leads to the phosphorylation and activation of STAT3 transcription factor. It is believed that the peptides and peptidomimetics provided herein can act as dominant negative inhibitors of the cytoplasmic domains, or as inhibitors of the cytokine dimerization and assembly.

The sequences of IL10, IL10R1, and IL10R2 are known in the art, and available in publicly accessible databases, for example, UniGene Accession Nos. Hs.193717, Hs.504035, and Hs.654593. Similarly, IFN-gamma, IFNGR1, and IFNGR2 are known proteins and receptors, the sequences of which are available to the public (e.g., UniGene Accession Nos. Hs.856, Hs.520414, and Hs.634632).

The family of STAT proteins also are well known in the art. In particular, STAT1 and STAT3 are provided by UniGene Accessions Hs.642990 and UniGene Accession Hs.463059, respectively.

A peptide or peptidomimetic is considered to inhibit cytokine signaling if, in the presence of the peptide or peptidomimetic, the binding of the cytokine (e.g., IFN-gamma or IL10) to its receptor is reduced to any degree as compared to the binding of cytokine to its receptor in the absence of the peptide or peptidomimetic. A peptide or peptidomimetic also is considered to inhibit cytokine signaling if, in the presence of the peptide or peptidomimetic, the phosphorylation of the target STAT protein is reduced to any degree as compared to the binding of cytokine to its receptor in the absence of the peptide or peptidomimetic. With respect to IFN-gamma, the target STAT protein is STAT1. With respect to IL10, the target STAT protein is STAT3. Assays and tests to measure or otherwise compare cytokine signaling or STAT activation are known in the art, some of which are illustrated herein.

A peptide or peptidomimetic is considered to inhibit the activation of a STAT protein if, in the presence of the peptide or peptidomimetic, STAT binding to a STAT target (e.g., another STAT protein, a protein other than STAT, or a nucleic acid) is reduced to any degree as compared to the binding of STAT to the same target in the absence of the peptide or peptidomimetic. Preferably, the peptide or peptidomimetic inhibits STAT activity to a degree sufficient to inhibit STAT regulation of genes, reduce the rate of cell growth of a cancer cell, and/or induce cell death of a cancer cell. Gene targets of STAT may include Activating transcription factor 3 (ATF3), Axin1 up-regulated 1 (AXU1), Nuclear receptor subfamily 4 group A member 1 (NR4A1), Basic helix-loop-helix domain containing, class 2 (STRA13), Growth arrest and DNA damage-inducible, alpha (GADD45A), Cell death-inducing DFFA-like effector B (CIDEB), FBJ murine osteosarcoma viral oncogene homolog B (FOSB), Dual specificity phosphatases 4 (DUSP4), Early growth response 2 (EGR2) and 3 (EGR3), CDC-like kinase-1 (CLK-1). Thus, the peptide or peptidomimetic can be used to regulate (e.g., upregulate or downregulate) the expression of such genes. STAT targets also may include histone deacetylases (e.g., HDAC1) and DNA methyltransferases (e.g., DNMT1), and the peptide or peptidomimetic can be used to inhibit the binding or other interaction between a STAT protein (e.g., STAT1 or STAT3) and one or both of these targets. Suitable assays to test for such binding activity and inhibition are known in the art, including binding affinity assays, cell growth and cytotoxicity assays, and gene regulation assays (e.g., luciferase reporter assay).

According to one aspect of the invention, the peptide or peptidomimetic comprises the sequence $x^1VLx^4Fx^6K$ (SEQ ID NO: 1), wherein x can be any amino acid. Desirably, $x^1$ is S, T, or A; $x^4$ is V or L; and $x^6$ is E or K, wherein more preferred residues are underlined. For example, the peptide or peptidomimetic can comprise the sequence SVLLFKK (SEQ ID NO: 2). Other examples of such sequences comprise any of SEQ ID NOs: 3-7.

In another aspect of the invention, the peptide or peptidomimetic comprises the sequence $LHGSTx^6SGFGSx^{12}K$ (SEQ ID NO: 75) or $LHGSTx^6SGFGSx^{12}KPSLQx^{18}$ (SEQ ID NO: 8), wherein x can be any amino acid. Desirably, $x^6$ is D or N, $x^{12}$ is T, A, or G, and $x^{18}$ (if present) is T or N, with preferred residues underlined. By way of further illustration, such a peptide can comprise the sequence LHGSTx-SGFGSTKPSLQT (SEQ ID NO: 9), wherein $x^6$ is D or N. More specific examples of such peptides comprise any of SEQ ID NOs: 10-16 and 72.

According to another aspect of the invention, the peptide or peptidomimetic comprises the sequence TDSGICLQ (SEQ ID NO: 17). By way of further illustration, such a peptide or peptidomimetic can comprise any of SEQ ID NOs: 18 or 19.

According to another aspect of the invention, the peptide or peptidomimetic comprises the sequence $Fx^2GYx^5x^6QTR$ (SEQ ID NO: 20), wherein x can be any amino acid. Desirably, $x^2$ is Q or R; $x^5$ is L or Q; and $x^6$ is R or K, wherein more preferred residues are underlined. By way of further example, such a peptide can comprise any of SEQ ID NOs: 21-24.

According to another aspect of the invention, the peptide or peptidomimetic comprises the sequence AxGYLKQ (SEQ ID NO: 25), wherein x can be any amino acid. Desirably, x is K, A, or T, preferably K. By way of further illustration, such a peptide can comprise any of SEQ ID NOs: 26-30.

According to another aspect of the invention, the peptide or peptidomimetic comprises the sequence LVTLPLISSL (SEQ ID NO: 31). By way of further illustration, such a peptide can comprise any of SEQ ID NOs: 32-35.

According to another aspect of the invention, the peptide or peptidomimetic comprises the sequence $Px^2HLKEx^7L$ (SEQ ID NO: 36), wherein x can be any amino acid. Desirably, $x^2$ is E or Q, and $x^7$ is Y or F. One example of such a peptide comprises the sequence of SEQ ID NO: 37.

According to another aspect of the invention, the peptide or peptidomimetic comprises the sequence SEFDI-FINYIEAY (SEQ ID NO: 38), optionally as a dimeric compound. For instance, the dimeric compound can comprise two regions, each comprising the sequence of SEQ ID NO: 38, and a linker joining the two regions. Such a compound is illustrated in the Examples.

According to another aspect of the invention, the peptide or peptidomimetic comprises the sequence $x^1LPKSL$ (SEQ ID NO: 39) or $x^1LPKSLx^7SVV$ (SEQ ID NO: 40), wherein x can be any amino acid. Desirably, $x^1$ is I, K, or M and $x^7$ is L or I. By way of further illustration, the peptide or peptidomimetic can comprise the sequence of any of SEQ ID NOs: 41-47.

According to another aspect of the invention, the peptide or peptidomimetic comprises the sequence YHSRx (SEQ ID NO: 48), wherein x can be any amino acid. Desirably, x is N, S, or D, preferably N or S. By way of further illustration, such a peptide or peptidomimetic can comprise the sequence of SEQ ID NO: 49, 50, 51, or 70.

According to another aspect of the invention, the peptide or peptidomimetic comprises the sequence of GYDKPH (SEQ ID NO: 52); GYDKPHx (SEQ ID NO: 53); GYDKPHxLV (SEQ ID NO: 54); or GYDKPHxLVD (SEQ ID NO: 55), wherein x can be any amino acid. Desirably, x is V or M, preferably V. By way of further illustration, the peptide or peptidomimetic can comprise the sequence of any of SEQ ID NOs: 56-59.

According to another aspect of the invention, the peptide or peptidomimetic comprises the sequence of GKESLx$^6$GYR (SEQ ID NO: 60) or GKESLx$^6$GYRx$^{10}$T (SEQ ID NO: 61), wherein x can be any amino acid. Desirably, $x^6$ is I or M (preferably I), and $x^{10}$ is L or P (preferably P). By way of further illustration, such a peptide can comprise the sequence of any of SEQ ID NOs: 62-64 and 71.

According to another aspect of the invention, the peptide or peptidomimetic comprises the sequence of $x^1Px^3x^{41}P$ (SEQ ID NO: 65) or $x^1Px^3x^{41}Px^7x^8x^9Ex^{11}YLx^{14}x^{15}P$ (SEQ ID NO: 66), wherein x can be any amino acid. Desirably, $x^1$ is T, S, A, or P; $x^3$ is P, Y, or L; $x^4$ is N, R, or S; $x^7$ is P, S, E, V, or L; $x^8$ is D, H, or Q; $x^9$ is I or E; $x^{11}$ is E or Q; $x^{14}$ is Q, R, or K; and $x^{15}$ is E or D. By way of further illustration, such a peptide can comprise the sequence of SEQ ID NO: 67 or 68.

According to another aspect of the invention, the peptide or peptidomimetic comprises the sequence VQRKAIHELIQVMAELSPAAKT (SEQ ID NO: 69) or VQRKAIHELIQVx$^{13}$AELSPAAKT (SEQ ID NO: 110), wherein $x^{13}$ is norleucine, optionally as a dimeric compound. The peptide or peptidomimetic alternatively can comprise the sequence SEFDIFINYIEAY (SEQ ID NO: 73), optionally as a dimeric compound. By way of further illustration, such a peptide or peptidomimetic can comprise SEQ ID NO: 74.

If the above-described peptide or peptidomimetic is a dimeric compound, it comprises two regions. For example, each region can comprise the sequence of SEQ ID NO: 69 or 110, and a linker joining the two regions, or each region can comprise the sequence of SEQ ID NO: 73, and a linker joining the two regions. Such compounds are illustrated in the Examples.

The peptide or peptidomimetic can comprise the inverse sequence of any of the sequences described herein. Furthermore, any of the foregoing sequences can be cyclized by known methods. For instance, cysteine, lysine, and/or glutamic acid residues can be introduced at desired positions of cyclization.

Variant sequences other than those specifically mentioned herein are contemplated, which comprise significant sequence identity to the disclosed amino acid sequences (e.g., 80%, 85%, 90%, 95%, 98%, or 99% sequence identity) and retain the ability to inhibit cytokine signaling and/or STAT protein activation. Such variants comprise one or more amino acid substitutions, deletions, or insertions as compared to the parent amino acid sequence. Conservative amino acid substitutions are known in the art, and include amino acid substitutions in which one amino acid having certain physical and/or chemical properties is exchanged for another amino acid that has the same or similar chemical or physical properties. For instance, the conservative amino acid substitution can be an acidic amino acid substituted for another acidic amino acid (e.g., Asp or Glu), an amino acid with a nonpolar side chain substituted for another amino acid with a nonpolar side chain (e.g., Ala, Gly, Val, Ile, Leu, Met, Phe, Pro, Trp, Val, etc.), a basic amino acid substituted for another basic amino acid (Lys, Arg, etc.), an amino acid with a polar side chain substituted for another amino acid with a polar side chain (Asn, Cys, Gln, Ser, Thr, Tyr, etc.), etc.

The peptide or peptidomimetic also can comprise synthetic, non-naturally occurring amino acids. Such synthetic amino acids include, for example, aminocyclohexane carboxylic acid, norleucine, α-amino n-decanoic acid, homoserine, S-acetylaminomethyl-cysteine, trans-3- and trans-4-hydroxyproline, 4-aminophenylalanine, 4-nitrophenylalanine, 4-chlorophenylalanine, 4-carboxyphenylalanine, β-phenylserine β-hydroxyphenylalanine, phenylglycine, α-naphthylalanine, cyclohexylalanine, cyclohexylglycine, indoline-2-carboxylic acid, 1,2,3,4-tetrahydroisoquinoline-3-carboxylic acid, aminomalonic acid, aminomalonic acid monoamide, N'-benzyl-N'-methyl-lysine, N',N'-dibenzyl-lysine, 6-hydroxylysine, ornithine, α-aminocyclopentane carboxylic acid, α-aminocyclohexane carboxylic acid, α-aminocycloheptane carboxylic acid, α-(2-amino-2-norbornane)-carboxylic acid, α,γ-diaminobutyric acid, α,β-diaminopropionic acid, homophenylalanine, and α-tert-butylglycine.

The term "peptidomimetic" as used herein refers to a compound that comprises the same general structure of a corresponding polypeptide, but which includes modifications that increase its stability or biological function. For instance, the peptidomimetic can be a "reverso" analogue of a given peptide, which means that the peptidomimetic comprises the reverse sequence of the peptide. In addition, or instead, the peptidomimetic can comprise one or more amino acids in a "D" configuration (e.g., D-amino acids), providing an "inverso" analogue. Peptidomimetics also include peptoids, wherein the side chain of each amino acid is appended to the nitrogen atom of the amino acid as opposed to the alpha carbon. Peptoids can, thus, be considered as N-substituted glycines which have repeating units of the general structure of $NRCH_2CO$ and which have the same or substantially the same amino acid sequence as the corresponding polypeptide.

The peptide or peptidomimetic can comprise the indicated amino acid sequence(s) alone or as part of a larger sequence, which includes additional amino acid residues (e.g., one, two, three, four, five or more amino acid residues) flanking the indicated amino acid sequence to the amino-terminal side, carboxy-terminal side, or both. Any flanking sequences can be used, provided the additional amino acid sequences do not eliminate the ability of the peptide to inhibit cytokine signaling or STAT activation. Thus, for example, the peptide or peptidomimetic can comprise flanking sequences from the native molecule that the peptide or peptidomimetic is designed to mimic, in which case the flanking sequences, alone or together with the sequences specifically indicated herein, comprise a fragment of the native molecule (e.g., IL10R1, IL10R2, IFNGR1, IFNGR2, IL10, or IFN-gamma).

The peptide or peptidomimetic can comprise, consist essentially of, or consist of, any of foregoing sequences or variants thereof. The peptide or peptidomimetic consists essentially of the foregoing sequences if it does not comprise other elements that prevent the peptide from inhibiting cytokine signaling or STAT activation.

Smaller peptides and peptidomimetics are believed to be advantageous for inhibiting STAT function and to facilitate entry into a cell. Thus, the peptide or peptidomimetic preferably comprises fewer than about 40 amino acids, such as about 35 or fewer amino acids, about 25 or fewer amino acids, or even about 20 or fewer amino acids. Generally, however, the peptide or peptidomimetic will comprise at least about 8 amino acids, such as at least about 10 amino acids, or at least about 15 amino acids.

The peptide or peptidomimetic can be used alone, or it can be coupled to a peptide stabilizing motif that stabilizes the folding of the peptide, or a cell penetrating motif so as to more efficiently facilitate the delivery of the peptide to the interior of a cell. Thus, the peptide or peptidomimetic can be provided as part of a composition comprising the peptide and a peptide stabilizing or cell penetrating motif. Any of various peptide stabilizing or cell penetrating motifs known in the art can be used, such as lipids and fatty acids, peptide transduction domains (e.g., HIV-TAT, HSV Transcription Factor (VP22), and penetratin), and other types of carrier molecules (e.g., Pep-1).

According to one aspect of the invention, the peptide stabilizing or cell penetrating motif is a fatty acid or lipid molecule. The fatty acid or lipid molecule can be, for example, a palmitoyl group, farnesyl group (e.g., farnesyl diphosphate), a geranylgeranyl group (e.g., geranylgeranyl diphosphate), a phospholipid group, glycophosphatidylinositol, phosphatidylserine, phosphatidylethanolamine, sphingomyelin, phosphatidylcholine, cardiolipin, phosphatidylinositol, phosphatidic acid, lysophosphoglyceride, a cholesterol group, an acetyl group, and the like. Preferably, the fatty acid molecule is a $C_1$ to $C_{24}$ fatty acid, e.g., lauric acid, palmitic acid, myristic acid, stearic acid, oleic acid, linoleic acid, α-linoleic acid, linolenic acid, arachidonic acid, timnodonic acid, docosohexenoic acid, erucic acid, arachidic acid, behenic acid. More preferably, the fatty acid molecule is a $C_8$ to $C_{16}$ fatty acid.

The fatty acid or lipid molecule can be attached to any suitable part of the peptide or peptidomimetic. In a preferred embodiment of the invention, the fatty acid or lipid molecule is attached at the amino (N-) terminus, the carboxyl (C-) terminus, or both the N- and C-termini of the peptide or peptidomimetic. When the fatty acid or lipid molecule is attached at the C-terminus of the polypeptide or peptidomimetic, the fatty acid or lipid molecule preferably is modified, e.g., to include an amino group such as $NH_2(CH_2)_nCOOH$ or $CH_3(CH_2)_mCH(NH_2)COOH$, wherein each of n and m is, independently, 1 to 24, preferably 8 to 16. The fatty acid or lipid residue can advantageously be attached to a terminal lysine in the epsilon (ε) position.

According to another aspect of the invention, the cell penetrating motif is a peptide transduction domain (also known as protein transduction domains or PTDs). PTDs typically are fused to the STAT-inhibitory peptide or peptidomimetic. Thus, the peptide or peptidomimetic can be a fusion protein comprising the peptide or peptidomimetic and a PTD. Often, the fusion protein is cleaved inside of a cell to remove the cell penetrating motif.

The peptide or peptidomimetic can further comprise linking residues disposed between the amino acid sequence and the peptide stabilizing or cell penetrating motif. Illustrative examples of such linking residues include K, KK, RK, RQ, KQ, RQI, KQI, RQIK (SEQ ID NO: 108), and KQIK (SEQ ID NO: 109)

The peptide or peptidomimetic can be prepared by any method, such as by synthesizing the peptide or peptidomimetic, or by expressing a nucleic acid encoding an appropriate amino acid sequence in a cell and harvesting the peptide from the cell. Of course, a combination of such methods also can be used. Methods of de novo synthesizing peptides and peptidomimetics, and methods of recombinantly producing peptides and peptidomimetics are known in the art (see, e.g., Chan et al., *Fmoc Solid Phase Peptide Synthesis*, Oxford University Press, Oxford, United Kingdom, 2005; *Peptide and Protein Drug Analysis*, ed. Reid, R., Marcel Dekker, Inc., 2000; *Epitope Mapping*, ed. Westwood et al., Oxford University Press, Oxford, United Kingdom, 2000; Sambrook et al., *Molecular Cloning: A Laboratory Manual*, 3$^{rd}$ ed., Cold Spring Harbor Press, Cold Spring Harbor, N.Y. 2001; and Ausubel et al., *Current Protocols in Molecular Biology*, Greene Publishing Associates and John Wiley & Sons, NY, 1994).

The invention also provides a nucleic acid encoding the amino acid sequence of the peptide or peptidomimetic. The nucleic acid can comprise DNA or RNA, and can be single or double stranded. Furthermore, the nucleic acid can comprise nucleotide analogues or derivatives (e.g., inosine or phosphorothioate nucleotides and the like). The nucleic acid can encode the amino acid sequence of the peptide or peptidomimetic alone, or as part of a fusion protein comprising such sequence and a cell penetrating motif, as described herein. The nucleic acid encoding the amino acid sequence of the peptide or peptidomimetic can be provided as part of a construct comprising the nucleic acid and elements that enable delivery of the nucleic acid to a cell, and/or expression of the nucleic acid in a cell. Such elements include, for example, expression vectors and transcription and/or translation sequences. Suitable vectors, transcription/translation sequences, and other elements, as well as methods of preparing such nucleic acids and constructs, are known in the art (e.g., Sambrook et al., supra; and Ausubel et al., supra).

The present invention further provides an antibody to the peptide or peptidomimetic, or an antigen binding fragment or portion thereof (e.g., Fab, F(ab')$_2$, dsFv, sFv, diabodies, and triabodies). The antibody can be monoclonal or polyclonal, and of any isotype, e.g., IgA, IgD, IgE, IgG, IgM, etc. The antibody can be a naturally-occurring antibody, e.g., an antibody isolated and/or purified from a mammal, e.g., mouse, rabbit, goat, horse, chicken, hamster, human, etc. Alternatively, the antibody can be a synthetic or genetically-engineered antibody, e.g., a humanized antibody or a chimeric antibody. The antibody can be in monomeric or polymeric form. The antibody, or antigen binding portion thereof; can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), or element particles (e.g., gold particles). Such antibodies can be used for any purpose, such as to facilitate the detection or purification of a peptide or peptidomimetic described herein. Suitable methods of making antibodies are known in the art, including standard hybridoma methods, EBV-hybridoma methods, bacteriophage vector expression systems, and phage-display systems (see, e.g., Köhler and Milstein, *Eur. J. Immunol.*, 5, 511-519 (1976); Harlow and Lane (eds.), *Antibodies: A Laboratory Manual*, CSH Press (1988); C. A. Janeway et al. (eds.), *Immunobiology*, 5$^{th}$ Ed., Garland Publishing, New York, N.Y. (2001); Haskard and Archer, *J. Immunol. Methods*, 74(2), 361-67 (1984); Roder et al., *Methods Enzymol.*, 121, 140-67 (1986); Huse et al., *Science*, 246, 1275-81 (1989); Sambrook et al., supra; Ausubel et al., supra; and Knappik et al., *J. Mol. Biol.,* 296: 57-86 (2000)).

The peptide or peptidomimetic, nucleic acid, or antibody can be isolated. The term "isolated" as used herein encompasses compounds or compositions that have been removed from a biological environment (e.g., a cell, tissue, culture medium, body fluid, etc.), or otherwise increased in purity to any degree (e.g., isolated from a synthesis medium). Isolated compounds and compositions, thus, can be synthetic or naturally produced.

A cell comprising the peptide or peptidomimetic, or nucleic acid encoding the amino acid sequence of the peptide or peptidomimetic, also is provided herein. Such a cell includes, for example, a cell engineered to express a nucleic acid encoding the amino acid sequence of the peptide or peptidomimetic. Suitable cells include prokaryotic and eukaryotic cells, e.g., mammalian cells, yeast, fungi, and bacteria (such as *E. coli*). The cell can be in vitro, as is useful for research or for production of the peptide or peptidomimetic, or the cell can be in vivo, for example, in a transgenic mammal that expresses the peptide.

The peptide or peptidomimetic can be used for any purpose, but is especially useful for inhibiting IL10 signaling or STAT3 activation in a cell or inhibiting IFN-gamma signaling or STAT1 activation in a cell. Thus, provided herein is a method of inhibiting IL10 signaling or STAT3 activation in a cell, which method comprises administering a peptide or peptidomimetic described herein to a cell, especially a peptide comprising the amino acid sequence of any of SEQ ID NOs: 1-38 and 72-74, or inverse sequence thereof. Also provided herein is a method of inhibiting IFN-gamma signaling or STAT1 activation in a cell comprising administering to the cell a peptide or peptidomimetic described herein to the cell, especially a peptide comprising the amino acid sequence of any of SEQ ID NOs: 39-71 and 110 or inverse sequence thereof.

The peptide or peptidomimetic can be administered to the cell by any method. For example, the peptide or peptidomimetic can be administered to a cell by contacting the cell with the peptide or peptidomimetic, typically in conjunction with a regent or other technique (e.g., microinjection or electroporation) that facilitates cellular uptake. Alternatively, and preferably, the peptide or peptidomimetic is administered by contacting the cell with a composition comprising the peptide or peptidomimetic and a cell penetrating motif, as discussed herein.

Alternatively, the peptide can be administered by introducing a nucleic acid encoding the amino acid sequence of the peptide into the cell such that the cell expresses a peptide comprising the amino acid sequence. The nucleic acid encoding the peptide can be introduced into the cell by any of various techniques, such as by contacting the cell with the nucleic acid or a composition comprising the nucleic acid as part of a construct, as described herein, that enables the delivery and expression of the nucleic acid. Specific protocols for introducing and expressing nucleic acids in cells are known in the art (see, e.g., Sambrook et al. (eds.), supra; and Ausubel et al., supra).

The peptide, peptidomimetic, or nucleic acid can be administered to a cell in vivo by administering the peptide, peptidomimetic, nucleic acid, or pharmaceutical composition comprising the peptide, peptidomimetic, or nucleic acid to a host comprising the cell. The host can be any host, such as a mammal, preferably a human. Suitable methods of administering peptides, peptidomimetics, and nucleic acids to hosts are known in the art, and discussed in greater detail in connection with the pharmaceutical composition, below.

The cell can be any type of cell that comprises IFN-gamma or IL10 receptors and, thus, participates in IFN-gamma or IL10 signaling. Preferably, the cell is of a type associated with aberrant IL10 or IFN-gamma signaling, or is otherwise related to a disease or condition associated with aberrant IL10 or IFN-gamma signaling. For example, the cell can be an engineered cell that is designed to mimic a condition or disease associated with IL10 or IFN-gamma signaling, or the cell can be a cell of a patient afflicted with a disease or condition associated with IL10 or IFN-gamma signaling. In this sense, aberrant IL10 or IFN-gamma signaling includes signaling above or below levels that would be considered normal for a particular cell or tissue type. Cancer cells and cells involved in autoimmune or inflammatory responses are examples of cell types that can be used. The cell can be in vitro or in vivo in any type of animal, such as a mammal, preferably a human.

The method of inhibiting cytokine signaling or STAT activation in a cell can be used for any purpose, such as for the research, treatment, or prevention of diseases or conditions associated with aberrant cytokine signaling or STAT activation. Aberrant cytokine signaling and STAT activation (e.g., increased phosphorylation of STAT) has been linked to a large variety of diseases, including infectious diseases, autoimmune diseases, and cancer. By way of illustration, aberrant IL10 signaling and/or STAT3 activation is thought to be linked to infection by Epstein-Barr virus, Orf virus, bovine papular stomatitis virus, lumpy skin disease virus, cytomegaloviruses, HIV, Dengue virus, influenza virus, measles virus, hepatitis C, *Leishmania* spp., hepatitis B virus, and West Nile virus, as well as lupus nephritis, systemic lupus erythematosus, immune thrombocytopenic purpura, myastenia gravis, multiple sclerosis, psoriasis, type I diabetes, or inflammatory bowel disease. Aberrant IFN-gamma signaling and/or STAT1 activation also has be associated with autoimmune and autoinflammatory diseases, as well as various cancers. Without wishing to be bound by any particular theory, it is believed that IFN-gamma and IL10 cytokine signaling and/or STAT activation is a necessary component of cancer cells, and that the administration of the peptide or peptidomimetic inhibits such signaling and/or activation, thereby preventing the cancer cells from growing or surviving. Cancers include any type of cancer associated with aberrant IL10 or IFN-gamma signaling and/or STAT activation. Non-limiting examples of specific types of cancers include cancer of the head and neck, eye, skin, mouth, throat, esophagus, chest, bone, lung, colon, sigmoid, rectum, stomach, thyroid, prostate, breast, ovaries, kidney (renal), liver, pancreas, brain, intestine, heart, or adrenals and leukemia and lymphoma. More particularly, cancers include solid tumor, sarcoma, carcinomas, fibrosarcoma, myxosarcoma, liposarcoma, chondrosarcoma, osteogenic sarcoma, chordoma, angiosarcoma, endotheliosarcoma, lymphangiosarcoma, lymphangioendothelio sarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, Kaposi's sarcoma, pinealoma, hemangioblastoma, acoustic neuroma, oligodendroglioma, menangioma, melanoma, neuroblastoma, retinoblastoma, a blood-born tumor, acute lymphoblastic leukemia, acute lymphoblastic B-cell leukemia, acute lymphoblastic T-cell leukemia, acute myeloblastic leukemia, acute promyelocytic leukemia, acute monoblastic leukemia, acute erythroleukemic leukemia, acute megakaryoblastic leukemia, acute myelomonocytic leukemia, acutenonlymphocyctic leukemia, acute undifferentiated leukemia, chronic myelocytic leukemia, chronic lymphocytic leukemia, hairy cell leukemia, or multiple myeloma. See, e.g., *Harrison's Principles of Internal Medicine*, Eugene Braunwald et al., eds., pp. 491 762 (15th ed. 2001).

Any one or more of the compounds or compositions of the invention described herein (e.g., peptide or peptidomimetic, nucleic acid, antibody, or cell) can be formulated as a pharmaceutical composition comprising a compound of the invention and a pharmaceutically acceptable carrier. Furthermore, the compounds or compositions of the invention can be used in the methods described herein alone or as part of a pharmaceutical formulation.

The pharmaceutical composition can comprise more than one compound or composition of the invention. Alternatively, or in addition, the pharmaceutical composition can comprise one or more other pharmaceutically active agents or drugs. Examples of such other pharmaceutically active agents or drugs that may be suitable for use in the pharmaceutical composition include anticancer agents. Suitable anticancer agents include, without limitation, alkylating agents; nitrogen mustards; folate antagonists; purine antagonists; pyrimidine antagonists; spindle poisons; topoisomerase inhibitors; apoptosis inducing agents; angiogenesis inhibitors; podophyllotoxins; nitrosoureas; cisplatin; carboplatin; interferon; asparginase; tamoxifen; leuprolide; flutamide; megestrol; mitomycin; bleomycin; doxorubicin; irinotecan; taxol; geldanamycin (e.g., 17-AAG); and various anticancer peptides and antibodies.

The carrier can be any of those conventionally used and is limited only by physio-chemical considerations, such as solubility and lack of reactivity with the active compound(s), and by the route of administration. The pharmaceutically acceptable carriers described herein, for example, vehicles, adjuvants, excipients, and diluents, are well-known to those skilled in the art and are readily available to the public. It is preferred that the pharmaceutically acceptable carrier be one which is chemically inert to the active agent(s) and one which has no detrimental side effects or toxicity under the conditions of use.

The choice of carrier will be determined in part by the particular compound or composition of the invention and other active agents or drugs used, as well as by the particular method used to administer the compound and/or inhibitor. Accordingly, there are a variety of suitable formulations of the pharmaceutical composition of the present inventive methods. The following formulations for oral, aerosol, parenteral, subcutaneous, intravenous, intramuscular, interperitoneal, rectal, and vaginal administration are exemplary and are in no way limiting. One skilled in the art will appreciate that these routes of administering the compound of the invention are known, and, although more than one route can be used to administer a particular compound, a particular route can provide a more immediate and more effective response than another route.

Injectable formulations are among those formulations that are preferred in accordance with the present invention. The requirements for effective pharmaceutical carriers for injectable compositions are well-known to those of ordinary skill in the art (See, e.g., *Pharmaceutics and Pharmacy Practice*, J. B. Lippincott Company, Philadelphia, Pa., Banker and Chalmers, eds., pages 238-250 (1982), and *ASHP Handbook on Injectable Drugs*, Toissel, 4th ed., pages 622-630 (1986)).

Topical formulations are well-known to those of skill in the art. Such formulations are particularly suitable in the context of the present invention for application to the skin.

Formulations suitable for oral administration can consist of (a) liquid solutions, such as an effective amount of the inhibitor dissolved in diluents, such as water, saline, or orange juice; (b) capsules, sachets, tablets, lozenges, and troches, each containing a predetermined amount of the active ingredient, as solids or granules; (c) powders; (d) suspensions in an appropriate liquid; and (e) suitable emulsions. Liquid formulations may include diluents, such as water and alcohols, for example, ethanol, benzyl alcohol, and the polyethylene alcohols, either with or without the addition of a pharmaceutically acceptable surfactant. Capsule forms can be of the ordinary hard- or soft-shelled gelatin type containing, for example, surfactants, lubricants, and inert fillers, such as lactose, sucrose, calcium phosphate, and corn starch. Tablet forms can include one or more of lactose, sucrose, mannitol, corn starch, potato starch, alginic acid, microcrystalline cellulose, acacia, gelatin, guar gum, colloidal silicon dioxide, croscarmellose sodium, talc, magnesium stearate, calcium stearate, zinc stearate, stearic acid, and other excipients, colorants, diluents, buffering agents, disintegrating agents, moistening agents, preservatives, flavoring agents, and pharmacologically compatible excipients. Lozenge forms can comprise the active ingredient in a flavor, usually sucrose and acacia or tragacanth, as well as pastilles comprising the active ingredient in an inert base, such as gelatin and glycerin, or sucrose and acacia, emulsions, gels, and the like containing, in addition to the active ingredient, such excipients as are known in the art.

The compounds and compositions of the invention, alone or in combination with other suitable components, can be made into aerosol formulations to be administered via inhalation. These aerosol formulations can be placed into pressurized acceptable propellants, such as dichlorodifluoromethane, propane, nitrogen, and the like. They also may be formulated as pharmaceuticals for non-pressured preparations, such as in a nebulizer or an atomizer. Such spray formulations also may be used to spray mucosa.

Formulations suitable for parenteral administration include aqueous and non-aqueous, isotonic sterile injection solutions, which can contain anti-oxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The compounds and compositions of the invention can be administered in a physiologically acceptable diluent in a pharmaceutical carrier, such as a sterile liquid or mixture of liquids, including water, saline, aqueous dextrose and related sugar solutions, an alcohol, such as ethanol, isopropanol, or hexadecyl alcohol, glycols, such as propylene glycol or polyethylene glycol, dimethylsulfoxide, glycerol ketals, such as 2,2-dimethyl-1,3-dioxolane-4-methanol, ethers, such as poly(ethyleneglycol) 400, an oil, a fatty acid, a fatty acid ester or glyceride, or an acetylated fatty acid glyceride with or without the addition of a pharmaceutically acceptable surfactant, such as a soap or a detergent, suspending agent, such as pectin, carbomers, methylcellulose, hydroxypropylmethylcellulose, or carboxymethylcellulose, or emulsifying agents and other pharmaceutical adjuvants.

Oils, which can be used in parenteral formulations include petroleum, animal, vegetable, or synthetic oils. Specific examples of oils include peanut, soybean, sesame, cottonseed, corn, olive, petrolatum, and mineral. Suitable fatty acids for use in parenteral formulations include oleic acid, stearic acid, and isostearic acid. Ethyl oleate and isopropyl myristate are examples of suitable fatty acid esters.

Suitable soaps for use in parenteral formulations include fatty alkali metal, ammonium, and triethanolamine salts, and suitable detergents include (a) cationic detergents such as, for example, dimethyl dialkyl ammonium halides, and alkyl pyridinium halides, (b) anionic detergents such as, for example, alkyl, aryl, and olefin sulfonates, alkyl, olefin, ether, and monoglyceride sulfates, and sulfosuccinates, (c) nonionic detergents such as, for example, fatty amine oxides, fatty acid alkanolamides, and polyoxyethylenepolypropylene copolymers, (d) amphoteric detergents such as, for example, alkyl-b-aminopropionates, and 2-alkyl-imidazoline quaternary ammonium salts, and (e) mixtures thereof.

Preservatives and buffers may be used. In order to minimize or eliminate irritation at the site of injection, such compositions may contain one or more nonionic surfactants having a hydrophile-lipophile balance (HLB) of from about 12 to about 17. The quantity of surfactant in such formulations will typically range from about 5% to about 15% by weight. Suitable surfactants include polyethylene sorbitan fatty acid esters, such as sorbitan monooleate and the high molecular weight adducts of ethylene oxide with a hydrophobic base, formed by the condensation of propylene oxide with propylene glycol. The parenteral formulations can be presented in unit-dose or multi-dose sealed containers, such as ampoules and vials, and can be stored in a freeze-dried (lyophilized) condition requiring only the addition of the sterile liquid excipient, for example, water, for injections, immediately prior to use. Extemporaneous injection solutions and suspensions can be prepared from sterile powders, granules, and tablets of the kind previously described.

Additionally, the compounds of the invention, or compositions comprising such compounds, can be made into suppositories by mixing with a variety of bases, such as emulsifying bases or water-soluble bases. Formulations suitable for vaginal administration can be presented as pessaries, tampons, creams, gels, pastes, foams, or spray formulas containing, in addition to the active ingredient, such carriers as are known in the art to be appropriate.

The following examples further illustrate the invention but, of course, should not be construed as in any way limiting its scope.

Example 1

The following Example illustrates the use of peptides according to the invention to inhibit cytokine signaling.

Comparison of IL10R1, IL10R2, IFNGR1, and IFNGR2 sequences from different species allowed identification of conserved regions. Alignment of the relevant portions of the sequences are provided below, in which conserved regions are identified with underlining.

Regions labeled "A" on the alignments are believed to be involved in the interactions of the receptors with JAK1. Regions D and E of IL10R1 are believed to bind STAT3 upon phosphorylation of tyrosine residues that are a part of YXXQ motifs. Region D of IFNGR1 is thought to bind STAT1 and STAT5 upon phosphorylation of tyrosine. It is also believed to interact with SOCS3 that competes for this site with STAT1 and STAT5, thus, inhibiting phosphorylation and activation of transcription factors by IFNGR. The functions of the other highly conserved region of IL10R1 and IFNGR1 cytoplasmic domains are unknown.

Cytoplasmic domains of IL10R2 and INGR2 contain one conserved region each. In the case of INGR2, the conserved motif is believed to be involved in interactions with JAK2, while a similar region of IL10R2 is thought to interact with TYK2.

IL10R1 Alignment

```
                            A (JAK1-binding)
Q13651    IIFFAFVLLLSGALAYCLALQLYVRRRKKLPSVLLFKKPSPFIFISQRPSPETQDTIHPL    296  I10R1_HUMAN   (SEQ ID NO: 76)
D2I2R3    SIFFIFVLLLCGALAYCLALHLYVRRRKKLPSVLVFEKPQPSSFVSQLPCPEPQDAIHLL    288  D2I2R3_AILME  (SEQ ID NO: 77)
Q61727    SILVISMLLFCGILV-CLVLQWYIRHPGKLPTVLVFKKP-HDFFPANPLCPETPDAIHIV    297  I10R1_MOUSE   (SEQ ID NO: 78)
Q99ND6    SIFFLSILILCGALV-CLVLLWYIRHPGKLPAVLVFEKP-PDFLLANPRCPETLDDIHIL    296  Q99ND6_RAT    (SEQ ID NO: 79)
           *:.  :*::.* *. **.*  *:*: ***:**:*:**    :  ::  .**. * ** :

B
Q13651    DEEAFLKVSPELKNLDLHGSTDSGFGSTKPSLQTEEPQFLLPDPHPQADRTLGNGEPPVL    356  I10R1_HUMAN
D2I2R3    DEEAFPKVSPELKNSELHGSTDSGFGSAKPSLQNEEPQFLLPAPHPQAGGTVGKGAPLEL    348  D2I2R3_AILME
Q61727    DLEVFPKVSLELRDSVLHGSTDSGFGSGKPSLQTEESQFLLPGSHPQIQGTLGKEESPGL    357  I10R1_MOUSE
Q99ND6    DLEAFPKVSPELKDSDLHGSTDSGFGSGKPSLQTEESQFFLLDSHAQIQETLGKEGSSEL    356  Q99ND6_RAT
          * *.* *** **::. *********** *****.**.**:*   .*.*   *:*:   . *

C
Q13651    GDSCSSGSSNSTDSGICLQEPSLSPSTGPTWEQQVGSNSRGQDDSGIDLVQNSEGRAGDT    416  I10R1_HUMAN
D2I2R3    ESSCSGGSS--TDSGICLQEPRLSPGTGPSWKQQVGNSSQDQDDSGIGLVQNSEGQPGDG    406  D2I2R3_AILME
Q61727    QATC--GDN--TDSGICLQEPGLHSSMGPAWKQQLGYTHQDQDDSDVNLVQNSPGQPKYT    413  I10R1_MOUSE
Q99ND6    QDTC--GDN--TDSGICLQESSLHSSMGPPWKQQFGYTHQDQDDS--DLVQNSPGHPKHT    410  Q99ND6_RAT
           :*   *. . *********. *  .**.*:**.*  . :.****   .***** *:..

D(STAT3 binding)
Q13651    QGGSALGHHSPPEPEVPGEEDPAAVAFQGYLRQTRCAEEKATKTGCLEEESPLTDGLGPK    476  I10R1_HUMAN
D2I2R3    QGGSALGHVNPPGPEASGEEDPDSVAFRGYLKQTRCTEEKAAKTGCLEEESSSTDSLGPK    466  D2I2R3_AILME
Q61727    QDASALGHVCLLEPKAPEEKDQVMVTFQGYQKQTRWKAEAAGPAECLDEEIPLTDAFDPE    473  I10R1_MOUSE
Q99ND6    QDGSALGHGCLLEPEVPEEKDQVMVTFQGYQKQTRWKEEAAEP---LDGEIPLAEAFDPE    467  Q99ND6_RAT
          *..***** *    *:.*   *:.*  *:*:** *** * *    *:.*  . :::.*:

E(STAT3 binding)
Q13651    FGRCLVDEAGLHPPALAKGYLKQDPLEMTLASSGAPTGQWNQPTEEWSLLALSSCSDLGI    536  I10R1_HUMAN
D2I2R3    FRTCLDAEAGWPPPVPAKGYLKQDP-GMTVTPSGTSTGQWDQPMEEWSLLGLTSCGDLGE    525  D2I2R3_AILME
```

```
                                                                    -continued
Q61727    LGVHLQDDDLAWPPPALAAGYLKQESQGMASAPPGTPSRQWNQLTEEWSLLGVVSCEDLSI      533  I10R1_MOUSE
Q99ND6    LGVRLQGDSAWPPVALATGYLKQESQGMASAPPGTPSRQWNQLAEESSLLGVVSCEDLSI      527  Q99ND6_RAT
             :    *    :   . * . * ****:.    *:  :..*:.: **:*  ** ***.:  ** **.

F
Q13651    SDWSFAHDLAPLGCVAAPGGLLGSFNSDLVTLPLISSLQSSE                        578  I10R1_HUMAN
D2I2R3    SDWSLAHDLASLDCLAAPGSLLGSFDSNLVTLPLISSLHSNE                        567  D2I2R3_AILME
Q61727    ESWRFAHKLDPLDCGAAPGGLLDSLGSNLVTLPLISSLQVEE                        575  I10R1_MOUSE
Q99ND6    ESLGFAHELVPLDCGAASSGLLDSLGTNLVTLPLISSLQIEE                        569  Q99ND6_RAT
            ..:**.* .*.* **...**.*:::**********: .*

IFNGR1 Alignment

A (JAK1- binding)
P15260    KSKEVCITIFNS-SIKGSLWIPVVAALLLFLVLSLVFICFYIKKINPLKEKSIILPKSLI      288  INGR1_HUMAN    (SEQ ID NO: 80)
Q5RF03    KSKEVCITIFNS-SIKSSLWIPVVAALLLILVLSLVFICFYIKKINPLKEKSIILPKSLI      288  Q5RF03_PONAB   (SEQ ID NO: 81)
Q3ZBH1    KSDELCITFSDDNNTEDPVWIPIVAALLLFLVFALVVVCCIIKKFYPIKREGTKLPKSLL      285  Q3ZBH1_BOVIN   (SEQ ID NO: 82)
Q05FF3    KSEELCITFSDDSNTEDPVWIPIVAALVLFLVFALVVACCIFKKLNPIKPEGTKLPKSLL      285  Q05FF3_CEREL   (SEQ ID NO: 83)
D2H0U1    MSKELCITTSDD-RRMDSVWIPIVA-VLLFLVLMLVFVFCYTKKMNPCKRESIMLPKSLL      256  D2H0U1_AILME   (SEQ ID NO: 84)
P15261    KSKDVCIPPFHD-DRKDSIWILVVAPLTVFTVVILVFAYWYTKK-NSFKRKSIMLPKSLL      295  INGR1_MOUSE    (SEQ ID NO: 85)
Q9QZ62    TSKDACIPFLHD-DREESIWMLLVAPLLFLTIVVPALVCCYIKK-NPFKRKSIMLPKSLL      282  Q9QZ62_RAT     (SEQ ID NO: 86)
            *.: **. ..    ..:*. :** . :: :.  ..    **    .  *  :.  *****:

P15260    SVVRSATLETKPESKYVSLITSYQPFSLEKEVVCEE-PLSPATVPGMHTEDNPGKVEHTE     347  INGR1_HUMAN
Q5RF03    SVVRSATLETKPESKYVSLITSYQPSSLEKEVVCEG-PLSPATVPGMHTEDNPGKVEHTE     347  Q5RF03_PONAB
Q3ZBH1    SVVKNASSEAKFDSKIISPIT-YQPIAVENE------QLSPGTISSLHTEDNPGKVEH-G     337  Q3ZBH1_BOVIN
Q05FF3    SVVKNASSEARLDSKVISPIT-YQPITVENE------QLSPGTISSVHTEDDPGKVEH-G     337  Q05FF3_CEREL
D2H0U1    SVVKNASSETKSESKCISPIT-YQPIVPENEKMVWEEQLSPATVAGTPNEDNLGKMEHRE     315  D2H0U1_AILME
P15261    SVVKSATLETKPESK-YSLVTPHQPAVLESET-----VICEEPLSTVTAPDSPEAAEQ-E     348  INGR1_MOUSE
Q9QZ62    SVVKNATSETKPESK-YSLVTSCQPAVLENET-----VICEEHLSTVTTPDSLEAPEQ-E     335  Q9QZ62_RAT
          ***::*: *:: :**   * :* **  .*.*          :.  :.     *.     *:

B
P15260    ELSSITEVVTTEENIPDVVPGSHLTPIERESSSPLSSNQSEPGSIALNSYHSRNCSESDH     407  INGR1_HUMAN
Q5RF03    ELSSITEVVTTEENIPDMAPGSHLTPVERESSSPLSSNQSEPCSIALNSYHSRNCSDSDH     407  Q5RF03_PONAB
Q3ZBH1    DLSSEMEVVTIEENISDLAPCSPLTP-EREDSIHASSNQSESCSITLNAYHSRNGS----     392  Q3ZBH1_BOVIN
Q05FF3    DLSSEVEVVTIEENISDLVPCSPLTP-EREGSIHANSSQSEPCSITLNAYHSRNGS----     392  Q05FF3_CEREL
D2H0U1    DVSSEIEVVTIEENSDMALGSPLNPGMRENSVHSSSNQSEPCVVAFNSYHSRNGS----     371  D2H0U1_AILME
P15261    ELSKETKALEAGGSTSAMTDSPPTPTQRRSFSLLSSNQSGPC--SLTAYHSRNGS----     402  INGR1_MOUSE
Q9QZ62    ELSKGTVATVAEGNTSPETTDSPLTPVQSGHFSLSSSNQSGSC--SLTTYHSRDGS----     389  Q9QZ62_RAT
          ::*.   .    .  ..   . .  *      .*    .*.**     .  ::.:****: *

C (STAT1 and STAT5-binding)
P15260    SRNGFDTDSSCLESHSSLSDSEFPPNNKGEIKTEGQELITVIKAPTSFGYDKPHVLVDLL     467  INGR1_HUMAN
Q5RF03    SRNGFDTDSSCLESHSSLSDSEFPPNNKGEIKTEGQELITVIKAPTSFGYDKPHVLVDLL     467  Q5RF03_PONAB
Q3ZBH1    -------DSGLAVSDNCSS-SEFPPSNKTEVKTEGQDFITLRNTTTSFGYDKPHVLVDLL     444  Q3ZBH1_BOVIN
Q05FF3    -------DSGLVVSDNCSS-SEFPPSNKTEVKTEGQDFLTLRNTTTSFGYDKPHVLVDLL     444  Q05FF3_CEREL
D2H0U1    -------DSGVVESDGFLSDSEFPPNNKTEMKPEVQECVVLRNTITSFGYDKPHVLVDLP     424  D2H0U1_AILME
P15261    -------DSGLVGSGSSISDLESLPNNNSETKMAEHDPPPVRKAPMASGYDKPHVLVDVL     455  INGR1_MOUSE
Q9QZ62    -------DSGLVGTGSSISDSDFLPNNDSETKMADPAPTPVRKALTFSGYDKPHVLVDVP     442  Q9QZ62_RAT
                 **  :     .  *  : :  *.*  * *             :  ::   ******:***:

D
P15260    VDDSGKESLIGYRPTEDSKEFS                                           489  INGR1_HUMAN
Q5RF03    VDDSGKESLIGYRPTEDSKEFS                                           489  Q5RF03_PONAB
Q3ZBH1    VDEGGKESLIGYRLTADSREFS                                           466  Q3ZBH1_BOVIN
Q05FF3    VDEGGKESLIGYRLTADSREFS                                           466  Q05FF3_CEREL
D2H0U1    VGEGGKESLIGYRLTADS----                                           442  D2H0U1_AILME
P15261    VDVGGKESLMGYRLTGEAQELS                                           477  INGR1_MOUSE
Q9QZ62    VDGEGKESLIGYRLTGDTQELS                                           464  Q9QZ62_RAT
          *. *****:*** *   ::

IFNGR2 Alignment

P38484    SNIFRVGHLSNISCYETMADASTELQQVILISVGTFSLLSVLAGACFFLVLKYRGLIKYW    280  INGR2_HUMAN    (SEQ ID NO: 87)
A9CAZ7    SNIFRLGHLSNTSCYETMADASTELQQVILISVGTFSLLSVLAGACCFLVLKYRGLIKYW    279  A9CAZ7_PAPAN   (SEQ ID NO: 88)
B1MT61    SNVN--GHLSNTSCYKIMEDASTKLQQVILISVGTFSLMSVLAGACFFLVLKYRGLIKYW    278  B1MT61_CALMO   (SEQ ID NO: 89)
Q05FE9    ENVSRPGHLSNISCXETAADASVKLQQDILAAATTFLVLXVVVGSCLFLVLKYRGLVKHW    226  Q05FE9_CEREL   (SEQ ID NO: 90)
Q05FF0    ENISRPGHLSNISCCETAADASVKLQQDFLAAGTTFLVLSVVVGSCLFLVLRYRGLVKHW    233  Q05FF0_BOVIN   (SEQ ID NO: 91)
A0AAR5    ENISRSGHLSNISCSETTADASTKLQQVILIAVGTFLLLLVVVGACLFLVLKFRGLVKYW    284  A0AAR5_PIG     (SEQ ID NO: 92)
```

-continued

```
D2HCG2   YNISRPGHLSNVSCYETTMDATTKLQQVIVIAVGVFLSLLALAGACFFLVLRYKGLVKYW    256  D2HCG2_AILME   (SEQ ID NO: 93)
Q78EC1   KKIRPHGLLSNVSCHETTANASARLQQVILIPLGIFALLLGLIGACFTLFLKYQSRVKYW    275  Q78EC1_9MURI   (SEQ ID NO: 94)
Q5RL90   SRFHLIGLQTVPECYRTTISEATKAGYIVAIFMSVGLLLIVIIVG-FFCLWRNQKAIKYL    265  Q5RL90_CHICK   (SEQ ID NO: 95)
Q08B45   VIPDLTGETSHVVCAKTPGAPGVTADKVIFISVG-LIILCCIFLGFSYAFSRHRGRIKTW    278  Q08B45_XENLA   (SEQ ID NO: 96)
              *    :    *  .          .       :   :    .  . : :  :*

P38484   FHTPPSIPLQIEEYLKDPTQPILEALDKDSSPKDDVWDSVSIISFPEKEQEDVLQTL---    337  INGR2_HUMAN
A9CAZ7   FHTPPSIPLQIEEYLKDPTQPILEVLDKDSSPKDDVWDSVSIISFPEKEQEDVLQTL---    336  A9CAZ7_PAPAN
B1MT61   FHTPPSIPLQIEEYLKDPAQPILEALDKOSSPKDDVWDSVSIISLPEKGQEDVLQTH---    335  B1MT61_CALMO
Q05FE9   FHSPPSIPSQIEEYLKDPDQPILDALDKDSSPKDDAWDSVSIVTFPENEQEGSPQ-----    281  Q05FE9_CEREL
Q05FF0   FHSPPSIPSQIEEYLKDPAQPILDALDKDSSPKDDTWDSVSVVTFPENEQEGSPQSTLNQ    293  Q05FF0_BOVIN
A0AAR5   FHSPPRIPVQIEEYLKDPAQPILDALDKDSSSRDDAWDSVSIVSFPENHREDTLQSTLTQ    344  A0AAR5_PIG
D2HCG2   FHSPPSIPSQIEEYLKDPSLPALDKDTSPTDDANDSVSVISFAEKDRE---------    307  D2HCG2_AILME
Q78EC1   FQAPPNIPEQIEEYLKDPDQFILEVLDKDGSPKEDSWDSVSIISSPEKERDDVLQTP---    332  Q78EC1_9MURI
Q5RL90   SQPPLRIPSHFEEYLRDPSMPQLEVLENHDEDPQDLLTVVYTGEGSSAYGDMLDGNTCSH    325  Q5RL90_CHICK
Q08B45   LYPPYNIPPDIEQYLQEPPWNGHLEKSKELHSAEEQYDIISIVESES-------------    325  Q08B45_XENLA
            .*   **  .:*:**:*                ..:.     ::       :     .

P38484   ------------------------                                       337  INGR2_HUMAN
A9CAZ7   ------------------------                                       336  A9CAZ7_PAPAN
B1MT61   ------------------------                                       335  B1MT61_CALMO
Q05FE9   ------------------------                                       281  Q05FE9_CEREL
Q05FF0   SAGPSHQPTEGVLC----------                                       307  Q05FF0_BOVIN
A0AAR5   STVSSHKPMDGAPSANTAADVSVPV                                      369  A0AAR5_PIG
D2HCG2   ------------------------                                       307  D2HCG2_AILME
Q78EC1   ------------------------                                       332  Q78EC1_9MURI
Q5RL90   SSSSSRDVT---------------                                       334  Q5RL90_CHICK
Q08B45   ------------------------                                       325  Q08B45_XENLA
```

IL10R2 Alignment

```
Q08334   MVCLALLGCFALLWCVYKKTKYAFSPRNSLPQHLKEFLGHPHHNTLLFFSFPLSDENDVF    292  I10R2_HUMAN    (SEQ ID NO: 97)
A9CAZ5   VVCLALLGCFALLWCIYKKTKYTFSPGNSLPQHLKEFLGHPHHNTLLFFSFPLSDENDVF    292  A9CAZ5_PAPAN   (SEQ ID NO: 98)
B0VXG5   VVCLALLGCFTLLWYIYKKTKYAFCPGNSLPQHLKEFLGHPHHNTLLFLSFPFSDENDVF    292  B0VXG5_CALJA   (SEQ ID NO: 99)
B5SNH8   VAVLLLLGCFALLWCIYKKTKYAFSPGNSLPQHLKEFLGHPHHSTLLFFSFPLSDENEVF    292  B5SNH8_OTOGA   (SEQ ID NO: 100)
B8K1B4   VVFLVLLACFALLWCIYKKTKYTFSPGNALPQHLKEFLGNPHHGTRLFFSFPLLDENEVF    292  B8K1B4_RABIT   (SEQ ID NO: 101)
Q764M7   AAFLLLLGCFILLRCIYKKTKNAFPPPRNSLPQHLKEFLSHPHHSTLLLFSIPLSDENEVF    293  Q764M7_PIG     (SEQ ID NO: 102)
Q3HTU8   VA-LLLLGCSALWCLYKRTKHVFSPRNCLPQHLKEFLGHPHHNTLLFFPPSDENEVF      252  Q3HTU8_CANFA   (SEQ ID NO: 103)
Q61190   VVFLFLLGCFVVLWLIYKKTKHTFRSGTSLPQHLKEFLGHPHHSTFLLFSFPPPEEAEVF    292  I10R2_MOUSE    (SEQ ID NO: 104)
Q2PBB9   AVIISVPVCFFSFWYLYRFTKHVFFPSYIFPQHLKEFLSKPPSGSQFFSPVP-QEEHQFH    295  Q2PBB9_CHICK   (SEQ ID NO: 105)
D2DJQ2   LSAVIVVGMFYLGISIYKAAKYLFFPKYSFPEHLKEYLSQPFYSSPHLSTQGPDDVAEPY    295  D2DJQ2_XENTR   (SEQ ID NO: 106)
Q6DCU5   LSPVIIVGLFYLGSRINKVAKYLFVPKYSFPEHLKEYLSQPFYSPPHL-TQGPDDGGDPC    292  Q6DCU5_XENLA   (SEQ ID NO: 107)
          : :           : :  :*   * .      :*:****:*..    :    :   :

Q08334   DKLSVIAEDSESGKQNPGDSCSLGTPPGQGPQS---------------------------    325  I10R2_HUMAN
A9CAZ5   DKLSVIAEDSESSKQNPDDSCSLGTPPGQGPQS---------------------------    325  A9CAZ5_PAPAN
B0VXG5   DKLSVITEDSESGKQNPGDGRSLRTLPGQGSQS---------------------------    325  B0VXG5_CALJA
B5SNH8   DKLSVIIEDSESSKQNASDSCSFRTLSEEGP-----------------------------    323  B5SNH8_OTOGA
B8K1B4   DKLSVVAEDSEGSKQSPGESCGLGTLSGQEP-----------------------------    323  B8K1B4_RABIT
Q764M7   DKLSVITDASESHKQNSGAGCSLGAQCGQGSFELVSQEGTPSAECSDPFLLTSASEDDQR    353  Q764M7_PIG
Q3HTU8   DKLSVITQVSESSRQSSGNSCTPGTPSGQGSSELVPKEGANTQGCSTPLLLSPATEGHQS    312  Q3HTU8_CANFA
Q61190   DKLSIISEESEGSKQSPEDNCASEPPSDPGPRELESKDEAPSPPHDDPKLLTSTSEV---    349  I10R2_MOUSE
Q2PBB9   DWLTVISEEPKSQRDETVEEASKTAEHHQDSKQEISDSEILPPLERDQTLLTLQSG----    351  Q2PBB9_CHICK
D2DJQ2   GTLTLVSEENPEV-----------------------------------------------    308  D2DJQ2_XENTR
Q6DCU5   GTLTLVSEENLEV-----------------------------------------------    305  Q6DCU5_XENLA
```

Peptides were synthesized that mimic the conserved regions of IL10R1, IL10R2, IFNGR1, and IFNGR2 intracellular domains. To stabilize the native fold of the fragments and to make them cell-permeable, the peptide mimetics were conjugated to palmitic acid. This modification has been shown previously to stabilize the tertiary structure of protein fragments and to improve their potency dramatically (Timofeeva et al., *ACS Chem. Biol.,* 2, 21, 799-809 (2007); Remsberg et al., *J. Med. Chem.,* 50, 4534-4538 (2007); and Johannessen et al., *ChemBioChem* 12: 914-21 (2011)). The peptides are identified in Table 1.

Peptides designed to mimic conserved regions of the receptor sequences were tested for the ability to inhibit IL10 and IFN-gamma signaling. Inhibition of IL10 signaling was tested in a mouse mast cell line MC/9. MC/9 cells can maintain growth in the presence IL4 and IL10, but undergo apoptosis in the absence or in case of inhibition of one of the two cytokines (Thompson-Snipes et al., *J. Exp. Med.,* 173, 507-510 (1991)). Inhibition of IFN-gamma signaling was tested in breast cancer cell line MDA-MB-231 that can be grown in serum-free medium in the presence of IFN-gamma. Abrogation of IFN-gamma signaling or STAT1 activation causes cell death in this cell line. The results are presented in Table 1 and FIG. 1.

Peptides mimicking JAK1 binding sites of both receptors turned out to be potent inhibitors of signaling, but did not distinguish between the two receptors (Table 1). Similarly, peptides derived from JAK2 interacting motif of IFNGR2 and TYK2-interacting motif of IL10R2 turned out to be potent but non-selective in inhibition of cytokines signaling (Table 2).

TABLE 1

Inhibition of MDA-MB-231 breast cancer and mouse mast MC/9 cells growth by compounds mimicking JAK1-binding site.

| Compound | Sequence | SEQ ID | GI$_{50}$, MDA-MB-231, μM** | GI$_{50}$, MC/9, μM |
|---|---|---|---|---|
| IFNGR1-1 | ε-Pal-FYIKKINPLKEK<u>SIILPKS</u>-NH$_2$* | 43 | >25 | |
| IFNGR1-3 | ε-Pal-PLKEK<u>SIILPKS</u>LLSVVR-NH$_2$ | 44 | 0.050 | |
| IFNGR1-4 | ε-Pal-<u>ILPKS</u>LLSVVRSAT-NH$_2$ | 45 | 2.5 | |
| IFNGR1-17 | ε-Pal-KKEK<u>SIILPKS</u>LLSVVR-NH$_2$ | 46 | | |
| IFNGR1-18 | ε-Pal-KK<u>SIILPKS</u>LLSVVR-NH$_2$ | 47 | | |
| IL10R1-1 | Pal-LYVRRRKKLP<u>SVLLFKK</u>-NH$_2$ | 3 | 0.025 | 1 |
| IL10R1-3 | ε-Pal-KKLP<u>SVLLFKK</u>PS-NH$_2$ | 4 | 2.5 | 0.05 |
| IL10R1-9 | Ac-SP<u>KKFLLVS</u>PLKK-ε-Pal (All-D) | 5 | 1 | |
| IL10R1-10 | Ac-<u>KKFLLVS</u>PLKK-ε-Pal (All-D) | 6 | 1 | |
| IL10R1-11 | Ac-P<u>KKFLLVS</u>PLKK-ε-Pal (All-D) | 7 | 1 | |

*The regions believed to be involved in interactions with JAK1 are underlined.
**GI$_{50}$ (concentration causing 50% inhibition in cell growth) was determined by MTT assay after 48 hours exposure to the compounds.

TABLE 2

Inhibition of MDA-MB-231 breast cancer cell line growth by compounds mimicking JAK2 binding site.

| Compound | Sequence | SEQ ID | GI$_{50}$, μM |
|---|---|---|---|
| IFNGR2-1 | ε-Pal-KKYQSRVKYWFQAPPNIP | 66 | 5 |
| IFNGR2-2 | ε-Pal-KAPP-NIPEQIEEYLKDP | 67 | 0.05 |

TABLE 3

Inhibition of MDA-MB-231 breast cancer cell line growth by compounds mimicking conserved regions B, C, and D of IFNGR1.

| | Compound | Sequence | SEQ ID | GI$_{50}$, μM |
|---|---|---|---|---|
| Conserved region B | IFNGR1-8 | ε-Pal-KSIALNSYHSRN-NH$_2$ | 49 | 5 ± 1 |
| | IFNGR1-13 | ε-Pal-KLNSYHSRNGS-NH$_2$ | 50 | 4.5 |
| | IFNGR1-14 | ε-Pal-KLNSYHSRNGSES | 70 | |
| | IFNGR1-20 | ε-Pal-KSYHSRNGS-NH$_2$ | 51 | |
| Region C (STAT1-binding) | IFNGR1-7 | ε-Pal-KGYDKPHVLVDLLVD-NH$_2$ | 56 | 1 |
| | IFNGR1-12 | ε-Pal-KGYDKPHVLV-NH$_2$ | 57 | 0.6 |
| | IFNGR1-15 | ε-Pal-KGYDKPHV-NH$_2$ | 58 | 1.6 |
| | IFNGR1-16 | ε-Pal-KFGYDKPHV-NH$_2$ | 59 | 2.1 |
| Conserved region D | IFNGR1-6 | ε-Pal-KGKESLIGYRPT-NH$_2$ | 62 | 0.07 |
| | IFNGR1-10 | ε-Pal-KGGKESLIGYR-NH$_2$ | 63 | 2.5 |
| | IFNGR1-11 | ε-Pal-KGKESLIGYR-NH$_2$ | 64 | 2 |
| | IFNGR1-19 | ε-Pal-GKESLIGYRPT-NH$_2$ | 71 | |

TABLE 4

Compounds mimicking conserved regions of IL10R1.

| | Compound | Sequence | SEQ ID | GI$_{50}$, µM |
|---|---|---|---|---|
| Conserved region B | IL10R1-4 | Pal-LHGSTDSGFGSTK | 72 | |
| | IL10R1-5 | Pal-LHGSTDSGFGSTKPSLQT | 10 | 1 |
| | IL10R1-14 | Ac-EETQLSPKTSGFGSDTSGHLK-ε-Pal (All-D) | 11 | 1 |
| | IL10R1-15 | Ac-ETQLSPKTSGFGSDTSGHLK-ε-Pal (All-D) | 12 | >5 |
| | IL10R1-16 | Ac-TQLSPKTSGFGSDTSGHLK-ε-Pal (All-D) | 13 | |
| | IL10R1-17 | ε-Pal-KTQLSPKTSGFGSDTSGHL-NH$_2$ (All-D) | 14 | >5 |
| | IL10R1-18 | ε-Pal-KEETQLSPKTSGEGSDTSGHL-NH$_2$ (All-D) | 15 | >5 |
| | IL10R1-25 | ε-Pal-KTQLSPKTSGFGSNTSGHL-NH$_2$ (All-D) | 16 | |
| Conserved region C | IL10R1-23 | ε-Pal-KTCGDNTDSGICLQ-NH$_2$ (cyclic)* | 18 | |
| | IL10R1-2 | ε-Pal-KSCSSGSSNSTDSGICLQ (cyclic)* | 19 | |
| Region D, STAT3-binding | IL10R1-22 | ε-Pal-KFQGYLRQTR-NH$_2$ | 22 | |
| | IL10R1-24 | Pal-AFQGYLRQTR-NH$_2$ | 23 | |
| | IL10R1-26 | Ac-RTQRLYGQFK-ε-Pal (All-D) | 24 | |
| Region E, STAT3-binding | IL10R1-8 | ε-Pal-KPPALAKGYLKQ-NH$_2$ | 27 | 5 |
| | IL10R1-19 | ε-Pal-KPPALAKGYLKQE-NH$_2$ | 28 | |
| | IL10R1-20 | ε-Pal-KAKGYLKQ-NH$_2$ | 29 | |
| | IL10R1-21 | Pal-LAKGYLKQ-NH$_2$ | 30 | |
| Conserved Region F | IL10R1-7 | ε-Pal-KLVTLPLISSLQSSE-NH$_2$ | 32 | 5 |
| | IL10R1-27 | ε-Pal-KLVTLPLISSLQ-NH$_2$ | 33 | >5 |
| | IL10R1-28 | ε-Pal-KLVTLPLISSL-NH$_2$ | 34 | |
| | IL10R1-29 | ε-Pal-KNLVTLPLISSL-NH$_2$ | 35 | |

*IL10R1-23 and IL10R1-2 are cyclic peptides with a disulfide bond bridging the two cysteine residues.

Example 2

The following Example illustrates the use of peptides according to the invention to inhibit cytokine signaling.

Both IFN-gamma and IL10 monomers are L-shaped predominantly helical molecules that dimerize into a symmetrical dimer held together by the interactions of two C-terminal helixes (helix F and helix E) with a bundle of four N-terminal helixes, A, B, C and D (Zdanov et al., Protein Sci., 5, 1955-1962 (1996)). The C-terminal helix F is involved in extensive interactions with helixes B, C, and D. In addition, crystal structures of human and viral IL10 complexed with a soluble form of IL10-R1 suggest that residues Ser141, Asp144, and Glu151 of helix F are essential for the binding of IL10 to the receptor (Yoon et al., Structure, 13, 551-564 (2005); and Jones et al., Proc. Natl. Acad. Sci. U.S.A., 99, 9404-9409 (2002)).

To evaluate whether synthetic helix F analogs could interact with the corresponding cytokine, fluorescent derivatives of helix F were synthesized. The helix F analogs are described below.

to recombinant Epstein Barr virus (EBV) IL10 with Kd equal to 50 nM.

EBV IL10 and human IL10 have identical helix F, and the residues involved in interactions with helix F also are highly conserved. Consequently, derivatives of human IL10 effectively can be used to overcome suppression of immune responses produced by EBV and, thus, can serve as preventative and therapeutic agents in lymphomas.

Additional mimetics of helix F of IL10 were prepared using N-α,ε-di-Fmoc-L-lysine coupled to Rink amide resin for simultaneous generation of two identical peptide chains of the dimeric inhibitor. The crystal structure of IL10 suggests that two lobes of the dimer are positioned about 15 Å apart. To allow the inhibitor to interfere with the assembly of both halves of the dimer, a flexible spacer was introduced that was at least 15 Å long. One of the spacers was provided by reacting resin-coupled L-lysine with Fmoc-PEG4-COOH (IL10-HF-1, Scheme 1). The other consisted of two residues of beta-alanine (IL10-HF-2, Scheme 1). Amino-butyric acid (Aib) was added at the N-termini of peptide portions of the inhibitor to provide stability to the α-helical structures.

| Compound | Sequence | SEQ ID |
|---|---|---|
| IL10-HF-6 | Ac-C(Fluo)YKAx$^4$SEFDIFINYIEAYx$^{18}$Tx$^{20}$KIRN-NH$_2$ | 74 |
| IFNG-HF-6 | Ac-C(Fluo)VQRKAIHELIQVx$^{13}$AELSPAAKT-NH$_2$ | 110 | x residues = norleucine

Microscale theremophoresis studies showed that IFNG-HF-6 interacted with recombinant human IFN-gamma with unexpectedly high affinity. Similarly, concentration-dependent changes in fluorescence intensity of environment-sensitive fluorescein label demonstrated that IL10-HF-6 binds IFN-gamma forms a dimer that has a topology similar to that of IL10. IFN-gamma monomer contains six helixes. Four helixes from one subunit form a cleft that accommodates a C-terminal helix from the second subunit. Dimeric analogs of the C-terminal helix were prepared in a manner similar to that of IL10 (Scheme 1).

Scheme 1

IL10-HF-1

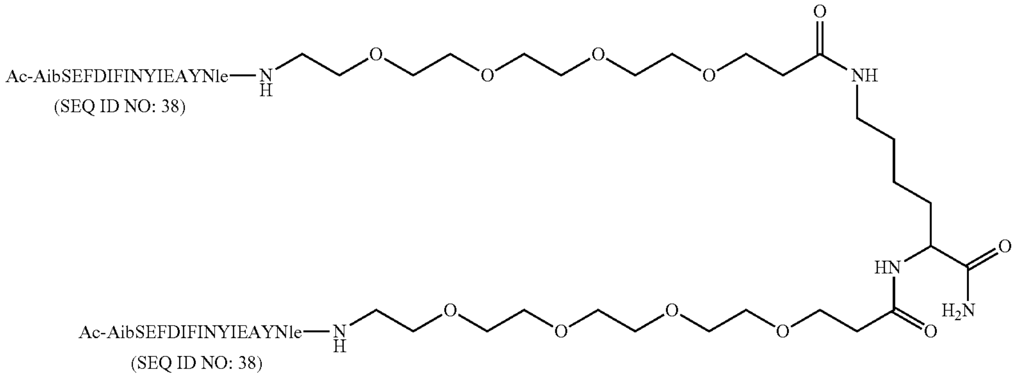

IL10-HF-2

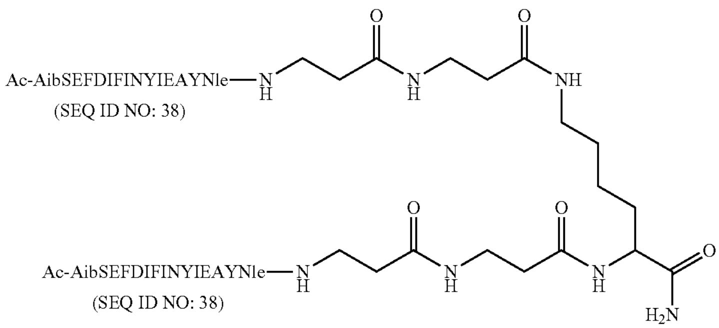

IFNG-HF-1

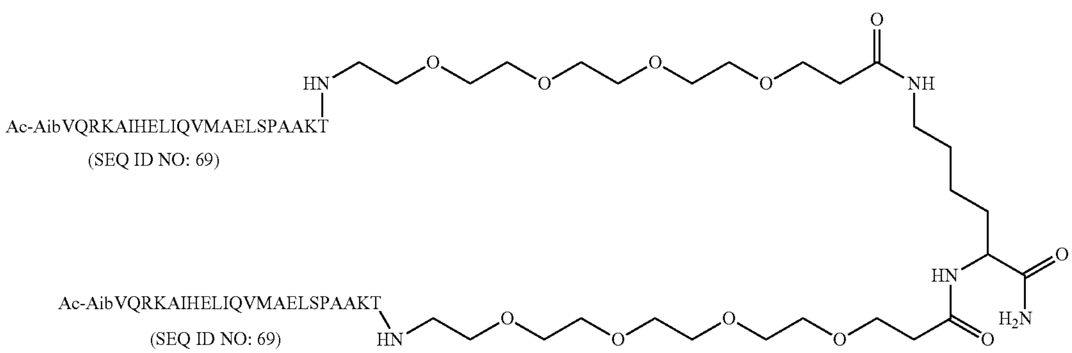

IFNG-HF-2

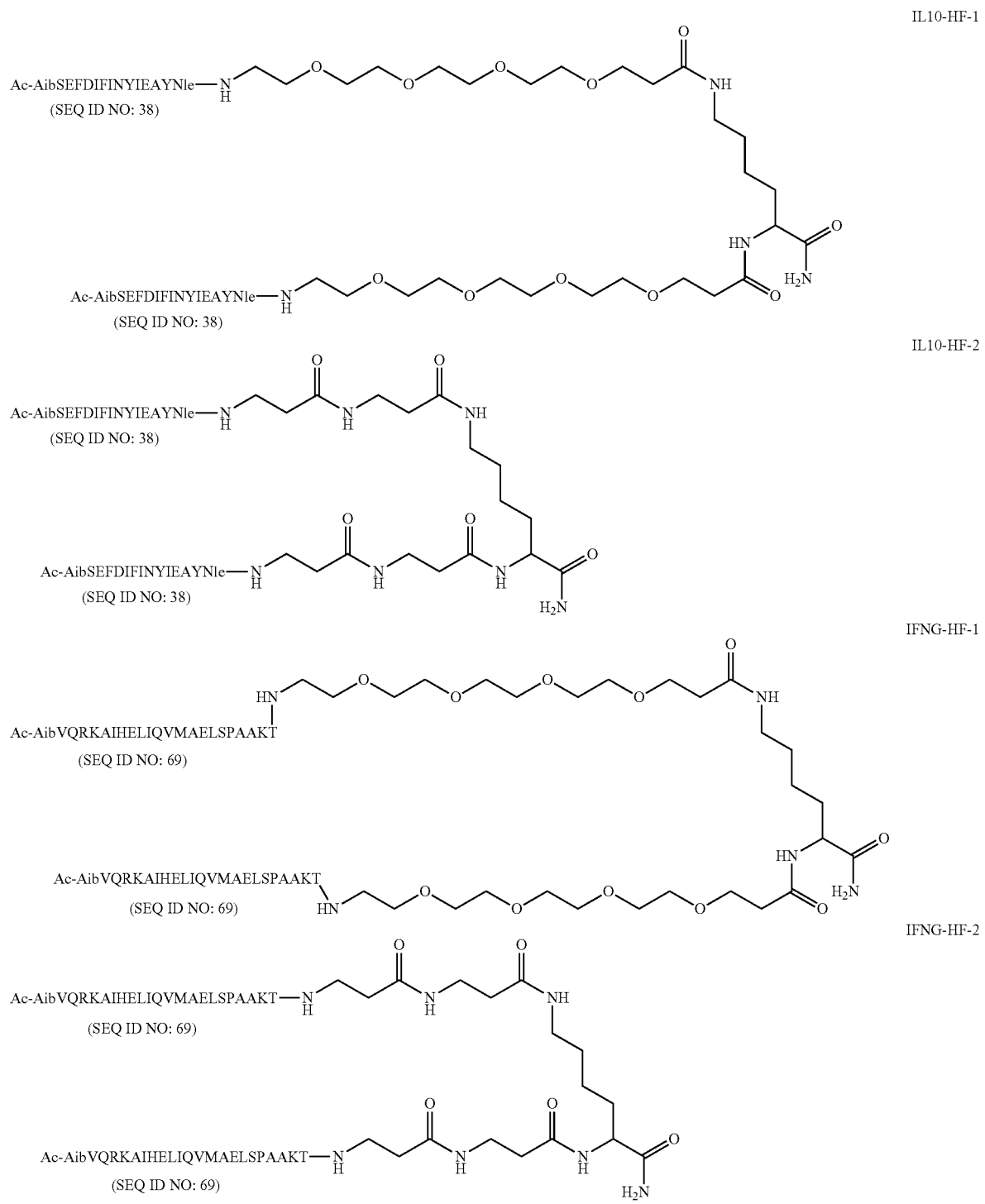

IFN-gamma binding to its receptor leads to phosphorylation and activation of transcription factor, STAT1. Therefore, STAT1 phosphorylation assays were used to characterize biological activity and selectivity of the IFN-gamma antagonists. Derivatives of IFN-gamma helix F inhibited phosphorylation of STAT1 in MDA-MB-231 breast cancer cells in a concentration-dependent manner. Dimeric inhibitor with a polyethylene glycol linker (IFNG-HF-1) completely abolished IFN-gamma activity at 100 nm.

While IL10-HF-1 compound potently inhibited IL10 dependent growth of mouse monocytes, it had no effect on IFN-gamma-dependent growth of tumor cells (FIG. 2). This result supports the selectivity of helix F-derived inhibitors.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A peptide or peptidomimetic comprising the amino acid sequence of any of SEQ ID NOs: 3-37, 72, and 74-75; wherein the peptide or peptidomimetic is 35 or fewer amino acid residues, wherein:
   SEQ ID NO: 20 is $Fx^2GYx^5x^6QTR$ (SEQ ID NO: 20), wherein $x^5$ is L; and $x^2$ and $x^6$ are any amino acid;
   SEQ ID NO: 25 is AxGYLKQ (SEQ ID NO: 25), wherein x is K or T; and
   SEQ ID NO: 36 is $Px^2HLKEx^7L$ (SEQ ID NO: 36), wherein $x^2$ is E or Q, and $X^7$ is Y or F.

2. The peptide or peptidomimetic of claim 1, wherein the peptide or peptidomimetic comprises the amino acid sequence of any of SEQ ID NOs: 3-37, 72, and 74-75, and inhibits IL10 signaling or STAT3 activation.

3. The peptide or peptidomimetic of claim 1, wherein the peptide or peptidomimetic comprises D-amino acids.

4. The peptide or peptidomimetic of claim 1 further comprising a cell-penetrating motif.

5. The peptide or peptidomimetic of claim 4, wherein the cell-penetrating motif is a protein transduction domain or fatty acid, optionally attached to the peptide or peptidomimetic via a linker sequence.

6. The peptide or peptidomimetic of claim 1, wherein the peptide or peptidomimetic comprises a terminal acetyl or palmitoyl group.

7. The peptide or peptidomimetic of claim 6, wherein the peptide or peptidomimetic comprises a terminal ε-palmitoyl modified lysine residue.

8. A pharmaceutical composition comprising the peptide or peptidomimetic of claim 1 and a carrier.

9. The peptide or peptidomimetic of claim 1 comprising the amino acid sequence of SEQ ID NOs: 20 or 25; wherein the peptide or peptidomimetic is 35 or fewer amino acid residues;
   SEQ ID NO: 20 is $Fx^2GYx^5x^6QTR$ (SEQ ID NO: 20), wherein $x^2$ is Q or R; $x^5$ is L; $x^6$ is R or K; and
   SEQ ID NO: 25 is AxGYLKQ (SEQ ID NO: 25), wherein x is K or T.

10. The peptide or peptidomimetic of claim 1, wherein the peptide or peptidomimetic comprises SEQ ID NO: 8.

11. The peptide or peptidomimetic of claim 1, wherein the peptide or peptidomimetic comprises $LHGSTx^6SGFGSx^{12}KPSLQx^{18}$ (SEQ ID NO: 8), wherein $x^6$ is D or N, $x^{12}$ is T, A, or G, and $x^{18}$ is T or N.

12. The peptide or peptidomimetic of claim 1, wherein the peptide or peptidomimetic comprises SEQ ID NO: 11.

13. The peptide or peptidomimetic of claim 1, wherein the peptide or peptidomimetic comprises SEQ ID NO: 31.

14. The peptide or peptidomimetic of claim 1, wherein the peptide or peptidomimetic comprises SEQ ID NO: 32.

15. A method of inhibiting IL10 signaling or STAT3 activation in a cell comprising introducing a peptide or peptidomimetic of claim 2 into the cell.

16. A method of treating a disease associated with IL10 signaling or STAT3 activation in a host comprising administering to the host a peptide or peptidomimetic of claim 2.

17. The method of claim 16, wherein the disease is an infectious disease, inflammatory disease, autoimmune disease, or cancer.

18. The method of claim 16, wherein the disease is an infection by Epstein-Barr virus, Orf virus, bovine papular stomatitis virus, lumpy skin disease virus, cytomegaloviruses, HIV, Dengue virus, influenza virus, measles virus, hepatitis C, *Leishmania* spp., hepatitis B virus, or West Nile virus.

19. The method of claim 16, wherein the disease is lupus nephritis, systemic lupus erythematosus, immune thrombocytopenic purpura, myasthenia gravis, multiple sclerosis, psoriasis, type I diabetes, or inflammatory bowel disease.

20. The method of claim 16, wherein the disease is prostate cancer, breast cancer, ovarian cancer, colon cancer, liver cancer, lung cancer, stomach cancer, renal cancer, pancreatic cancer, thyroid cancer, skin cancer, lymphoma, or leukemia.

* * * * *